US012576029B2

(12) United States Patent
Rudra et al.

(10) Patent No.: US 12,576,029 B2
(45) Date of Patent: Mar. 17, 2026

(54) NONCOMPETITIVE RECEPTOR-TARGETED VACCINE DELIVERY TO PLASMACYTOID DENDRITIC CELLS

(71) Applicant: Washington University, St. Louis, MO (US)

(72) Inventors: Shiva Kumar Jai Simha Rudra, St. Louis, MO (US); Zoe Clapacs, St. Louis, MO (US)

(73) Assignee: Washington University, St. Louis, MO (US)

( * ) Notice: Subject to any disclaimer, the term of this patent is extended or adjusted under 35 U.S.C. 154(b) by 307 days.

(21) Appl. No.: 18/221,262

(22) Filed: Jul. 12, 2023

(65) Prior Publication Data

US 2024/0024238 A1 Jan. 25, 2024

Related U.S. Application Data

(60) Provisional application No. 63/388,430, filed on Jul. 12, 2022.

(51) Int. Cl.
*A61K 9/1271* (2025.01)
*A61K 9/51* (2006.01)

(52) U.S. Cl.
CPC .......... *A61K 9/1271* (2013.01); *A61K 9/5161* (2013.01)

(58) Field of Classification Search
CPC .... A61K 9/127; A61K 9/1271; A61K 9/1272; A61K 9/1277
See application file for complete search history.

(56) References Cited

U.S. PATENT DOCUMENTS

| | | | | |
|---|---|---|---|---|
| 10,786,465 | B2 * | 9/2020 | Majeti | A61K 9/5192 |
| 2007/0116753 | A1 * | 5/2007 | Hong | A61P 31/04 424/450 |
| 2010/0069426 | A1 * | 3/2010 | Zale | A61P 35/00 514/772.3 |
| 2017/0296639 | A1 * | 10/2017 | Ma | A61K 39/001102 |
| 2018/0312536 | A1 * | 11/2018 | Sakamuri | C07K 16/3084 |
| 2019/0343965 | A1 * | 11/2019 | De Berardinis | C12N 7/00 |

OTHER PUBLICATIONS

Annie-Louise Robson et al. "Advantages and Limitations of Current Imaging Techniques for Characterizing Liposome Morphology." Frontiers in Pharmacology, vol. 9, Article 80, Feb. 2018, pp. 1-8. (Year: 2018).*

Joseph A. Katakowski et al. "Delivery of siRNAs to Dendritic Cells Using DEC205-Targeted Lipid Nanoparticles to Inhibit Immune Responses." Molecular Therapy, vol. 24, No. 1, Jan. 2016, pp. 146-155 and 2 pages of supplemental information. (Year: 2016).*

(Continued)

*Primary Examiner* — Isaac Shomer
(74) *Attorney, Agent, or Firm* — Polsinelli PC

(57) ABSTRACT

Disclosed herein are compositions comprising a hydrogel scaffold, methods of generating a hydrogel scaffold, and systems for and methods of using the hydrogel scaffold to produce biologically active molecules.

14 Claims, 19 Drawing Sheets
(5 of 19 Drawing Sheet(s) Filed in Color)

(56) References Cited

OTHER PUBLICATIONS

Maria Gregori et al. "Novel Antitransferrin Receptor Antibodies Improve the Blood-Brain Barrier Crossing Efficacy of Immunoliposomes." Journal of Pharmaceutical Sciences, vol. 105, 2016, pp. 276-283 and 4 pages of supplemental information. (Year: 2016).*

Elham Hatami, Meena Jaggia, Subhash C. Chauhan, Murali M. Yallapu. "Gambogic acid: A shining natural compound to nanomedicine for cancer therapeutics." BBA—Reviews on Cancer, vol. 1874, 2020, 188381, pp. 1-16. (Year: 2020).*

Ying Ji, Shuo Shan, Mingyu He, Chih-Chang Chu. "Inclusion complex from cyclodextrin-grafted hyaluronic acid and pseudo protein as biodegradable nano-delivery vehicle for gambogic acid." Acta Biomaterialia, vol. 62, 2017, pp. 234-245. (Year: 2017).*

Ravi Doddapaneni, Ketan Patel, Ibtisam Hasan Owaid, and Mandip Singh. "Tumor neovasculature-targeted cationic PEGylated liposomes of gambogic acid for the treatment of triple-negative breast cancer." Drug Delivery, vol. 23(4), 2016, pp. 1232-1241. (Year: 2016).*

Horisberger, Michel Andre & Di Marco, Stefania, "Interferon-alpha hybrids," Pharmacology & Therapeutics, 1995, vol. 66, issue 3, pp. 507-534.

* cited by examiner

NONCOMPETITIVE RECEPTOR-TARGETED VACCINE DELIVERY TO PLASMACYTOID DENDRITIC CELLS

1. CROSS-REFERENCE TO RELATED APPLICATIONS

The present application claims the benefit of U.S. Provisional Patent Application No. 63/388,430, entitled, "NON-COMPETITIVE RECEPTOR-TARGETED VACCINE DELIVERY TO PLASMACYTOID DENDRITIC CELLS" filed Jul. 5, 2023, the content of which is hereby incorporated by reference in its entirety.

II. FIELD OF TECHNOLOGY

This disclosure generally relates to methods, compositions, kits, and agents useful for targeting plasmacytoid dendritic cells. More specifically disclosed herein liposomes or nanoparticles which provides a non-competitive active targeted delivery to plasmacytoid dendritic cells.

III. BACKGROUND

Plasmacytoid dendritic cells (pDCs) are a rare yet crucial DC subset central to immunity, tolerance, and autoimmunity making them an attractive target for therapeutic delivery. However, their relative rarity in tissues (0.1-0.5%) makes this a challenging task. pDCs) play a unique role in responding to viral infection as the chief producers of interferon-alpha (IFNa), which is known to enhance development of cellular and humoral immunity. Prior pDC targeting efforts have relied either on non-specific receptors or passive morphology.

pDCs are a unique subset that specialize in sensing viral nucleic acids via toll-like receptors (TLRs) 7 and 9 and produce high levels of type-I interferons (IFNIs) that exert stimulatory effects on the adaptive immune system and induce potent anti-viral or anti-cancer immunity. To date, there are no vaccines targeting pDCs in the market but there is potential interest in developing alternates top DCs such as cell lines for personalized therapies which can be cost prohibitive.

To circumvent these limitations and make nonviral delivery applicable for pDCs, new targeting approaches need to be identified. Thus, there remains an unmet need to improve methods concerning targeted delivery to pDCs.

IV. SUMMARY

In some aspects, disclosed herein is a composition comprising liposomes, wherein the liposomes comprise a targeting moiety for delivery of the liposomes to plasmacytoid dendritic cells (pDCs). In some aspects, the targeting moiety is gambogic acid (GA). In some aspects, the targeting moiety results in enhanced delivery of the liposomes to pDCs cells, by at least by 25% compared to liposomes without the targeting moiety.

In some aspects, the liposome further comprises a therapeutic agent or a diagnostic agent. In some aspects, the therapeutic agent or a diagnostic agent is a nucleic acid, an antiviral agent, an antibacterial agent, an antifungal agent, an antimetabolic agent, an anticancer agent, anti-inflammatory agent, a polypeptide, a protein, or an imaging agent.

In further aspects, the disclosure encompasses a composition comprising liposomes, wherein the liposomes are functionalized with a targeting moiety, and wherein the targeting moiety binds CD71. In some aspects, the targeting moiety is GA. In some aspects, the targeting moiety results enhanced delivery of the liposomes to pDCs cells, by at least by 25% compared to liposomes without the targeting moiety.

In some aspects, the disclosed targeting moiety binds to CD71 non-competitively with a natural ligand of CD71. In some aspects, the targeting moiety binds to CD71 non-competitively with transferrin. In some aspects, the liposome further comprises a therapeutic agent. In some aspects, the therapeutic agent is a nucleic acid, an antiviral agent, an antibacterial agent, an antifungal agent, an antimetabolic agent, an anticancer agent, anti-inflammatory agent, a polypeptide, a protein, or an imaging agent.

Further encompassed in the disclosure is a pharmaceutical composition comprising the composition disclosed herein and a pharmaceutically acceptable carrier.

In further aspects, provided herein is a method of treating a subject in need thereof comprising administering an effective amount of a composition disclosed herein to treat, prevent, or reduce occurrence of a disease or disorder in a subject. In some aspects of the method, the disease or disorder is a cancer, autoimmune disease, inflammatory disease, viral infection, bacterial infection, or fungal infection.

V. BRIEF DESCRIPTION OF THE FIGURES

The patent or patent application file contains at least one drawing executed in color. Copies of this patent or patent application publication with color drawing(s) will be provided by the Office upon request and payment of the necessary fee.

Those of skill in the art will understand that the drawings, described below, are for illustrative purposes only. The drawings are not intended to limit the scope of the present teachings in any way.

FIG. 1A-IF show characterization of mice inbred lines. FIG. 1A show distribution of dendritic cells in bone marrow (BM), spleen (SPL), and lymph node (LN) of BL/6, 129SV, and BALB/C mice. FIG. 1B shows expression of CD71 on dendritic cells in bone marrow (BM), spleen (SPL), and lymph node (LN) of BL/6, 129SV, and BALB/C mice.

FIG. 1C shows the percentage of fraction of cell in the dendritic cell population in spleen, and lymph node of BL/6, 129SV, and BALB/C. FIG. 1D shows the median fluorescence intensity of dendritic cells in bone marrow (BM), spleen (SPL), and lymph node (LN) of BL/6, 129SV, and BALB/C mice. FIG. 1E shows pDC cell fraction in bone marrow (BM), spleen (SPL), and lymph node (LN) of BL/6, 129SV, and BALB/C mice. $p<0.001$, compared with each other using BL/6 as a reference, using two-way ANOVA. FIG. 1F shows median fluorescence intensity of pDC in bone marrow (BM), spleen (SPL), and lymph node (LN) of BL/6, 129SV, and BALB/C. $p<0.001$, compared with each other using BL/6 as a reference, using two-way ANOVA.

Figure 4A:
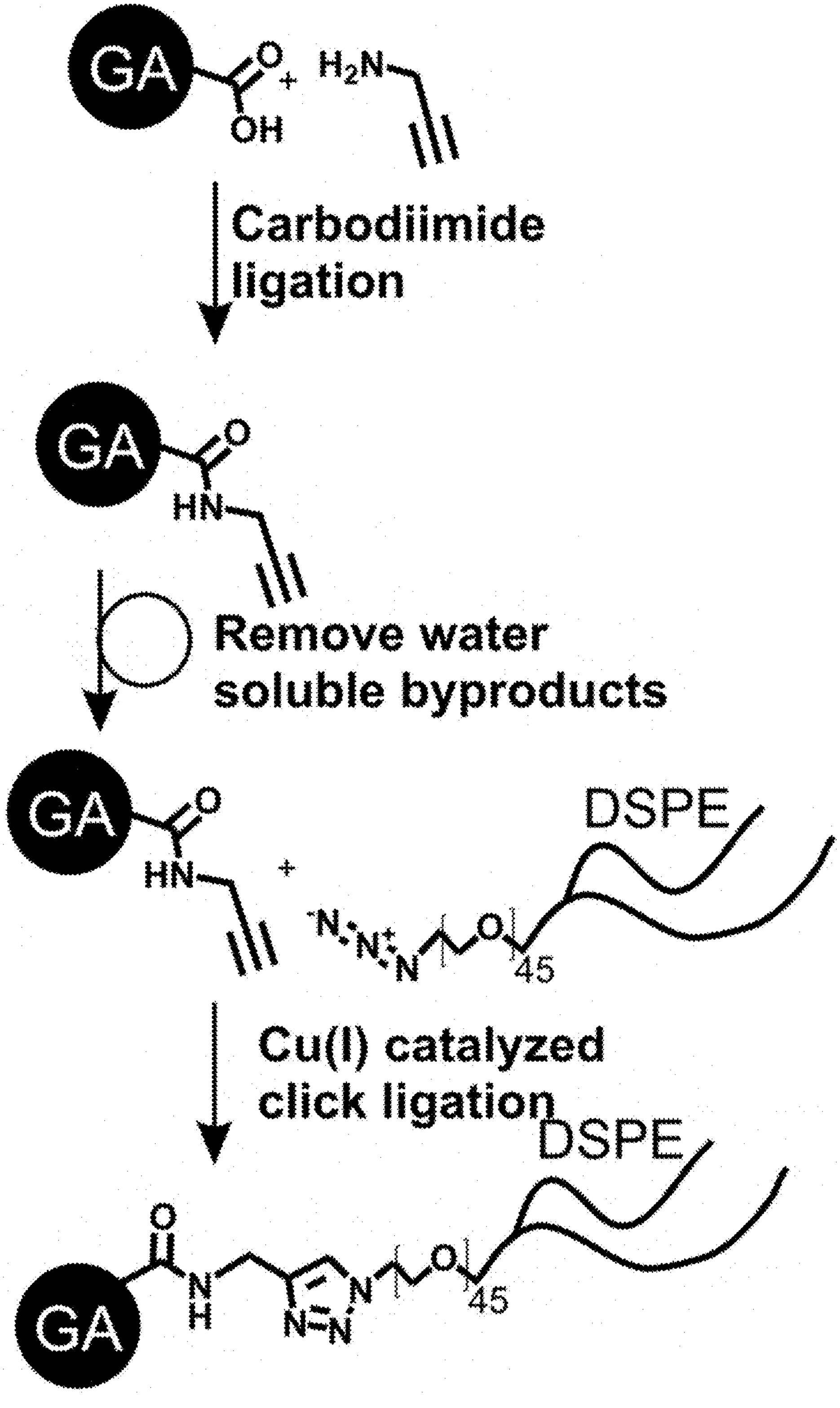
Figure 4B:
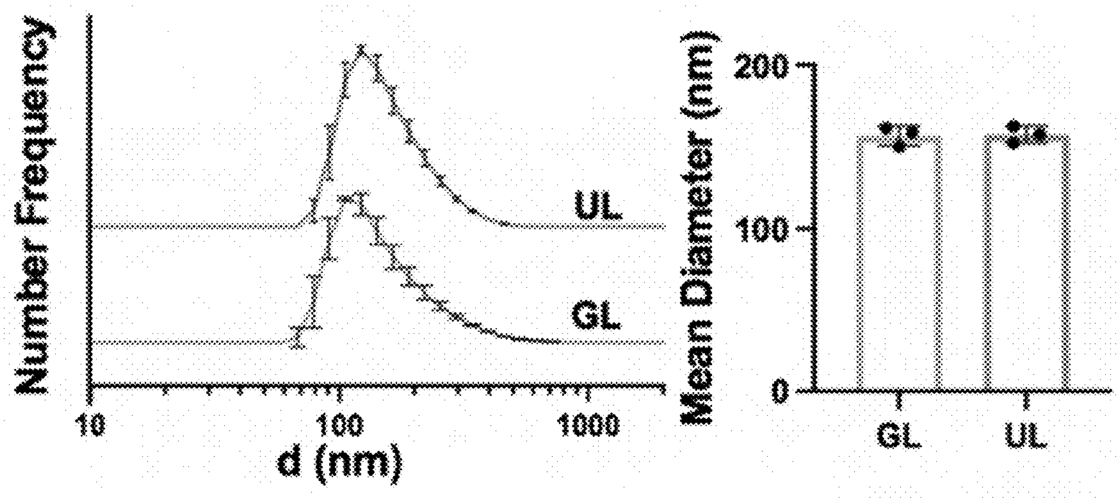
Figure 4C:
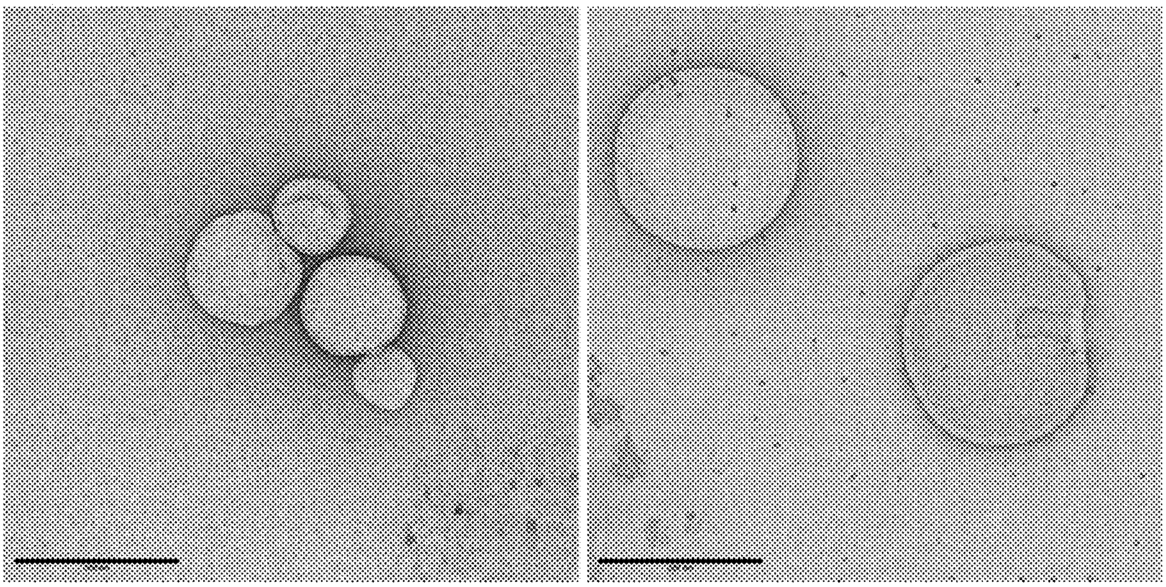
Figure 4D:
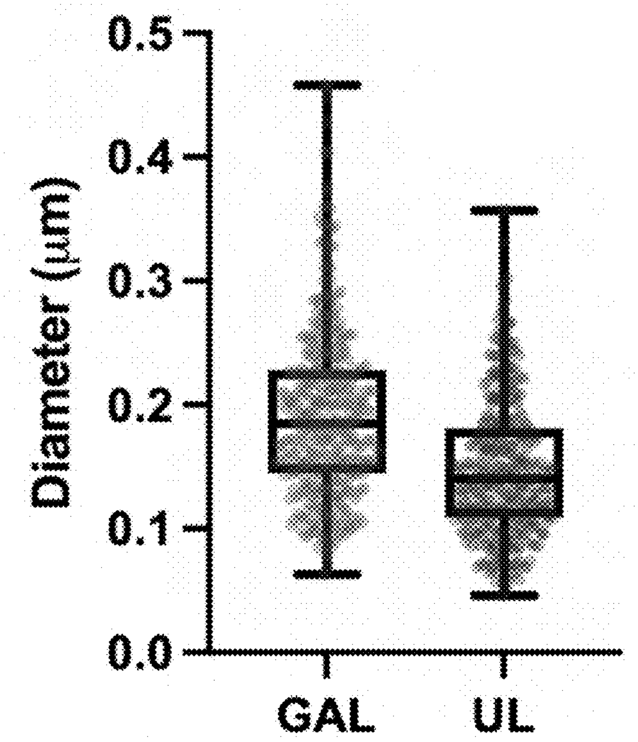

FIG. 4A-4D show synthesis and characterization of GA-liposomes. FIG. 4A show synthesis schematic of GA-PEG-DSPE through a 2-step ligation process using carbodiimide and Cu-catalyzed click reactions in sequence. FIG. 4B shows DLS analysis of liposome size. FIG. 4C show TEM micrographs of liposome. FIG. 4D show size and distribution of particle size.

Figure 5:
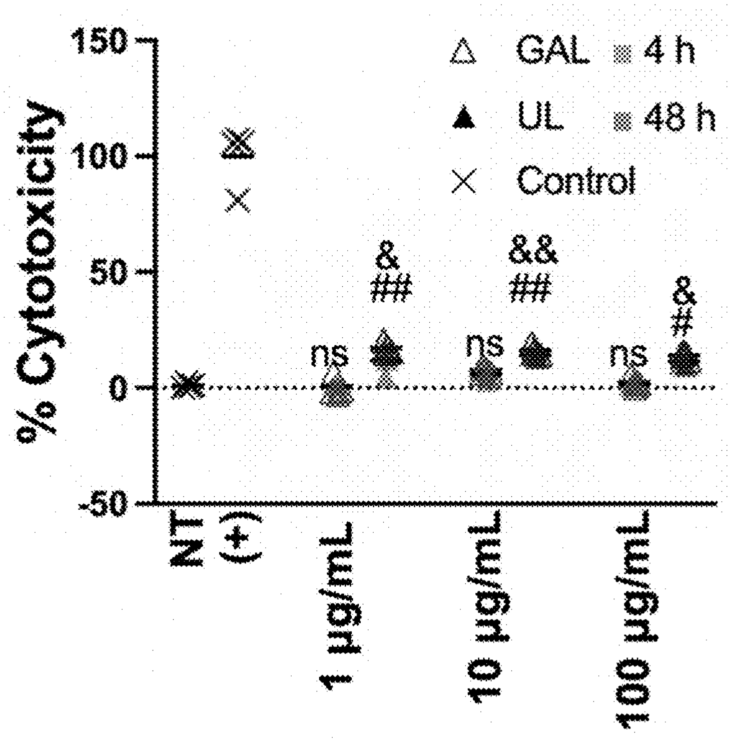

FIG. 5 shows GA functionalized liposomes induced minimal splenocyte.

Figure 6:
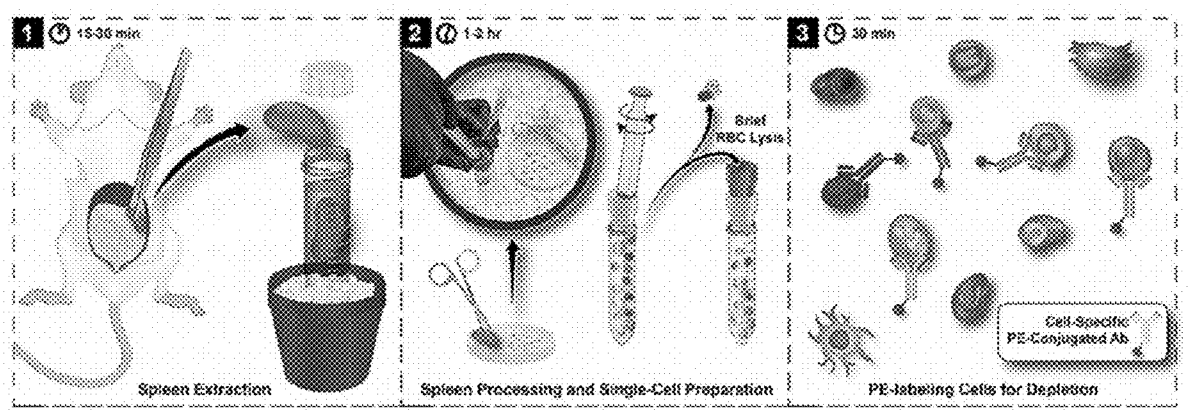

FIG. 6 shows the schematic of preparation of tissue for GA functionalized liposome uptake and flow.

Figure 7:
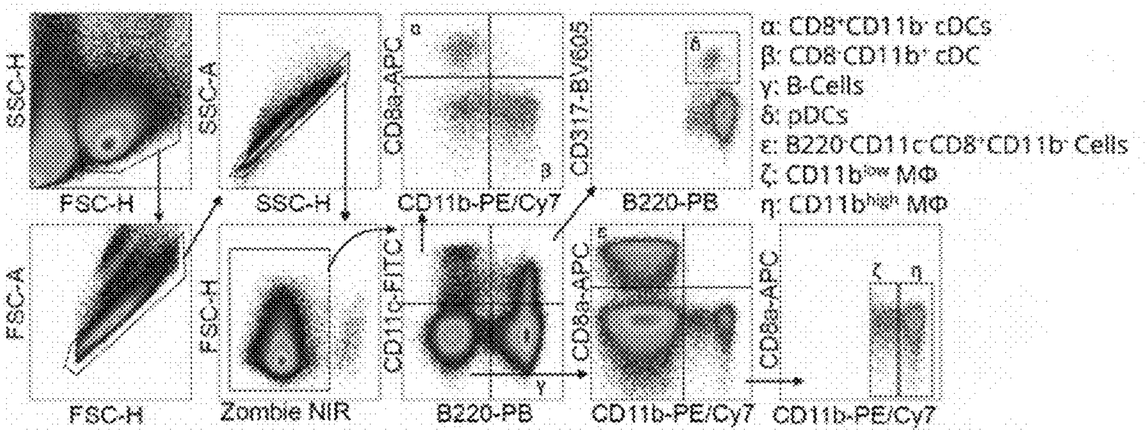

FIG. 7 shows populations of cells identified among cells isolated from spleen, bone marrow and lymph node.

Figure 8A:
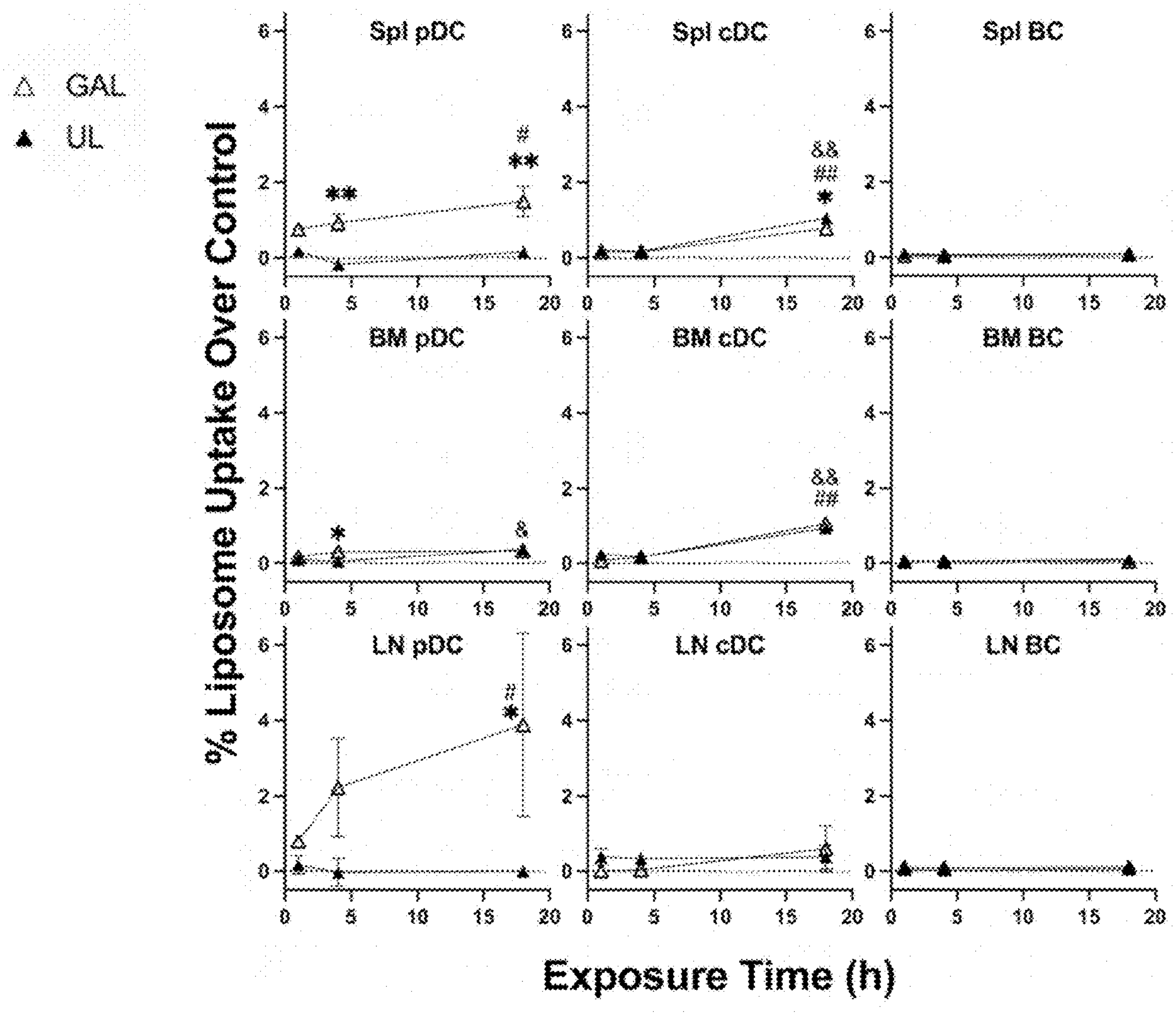
Figure 8B:
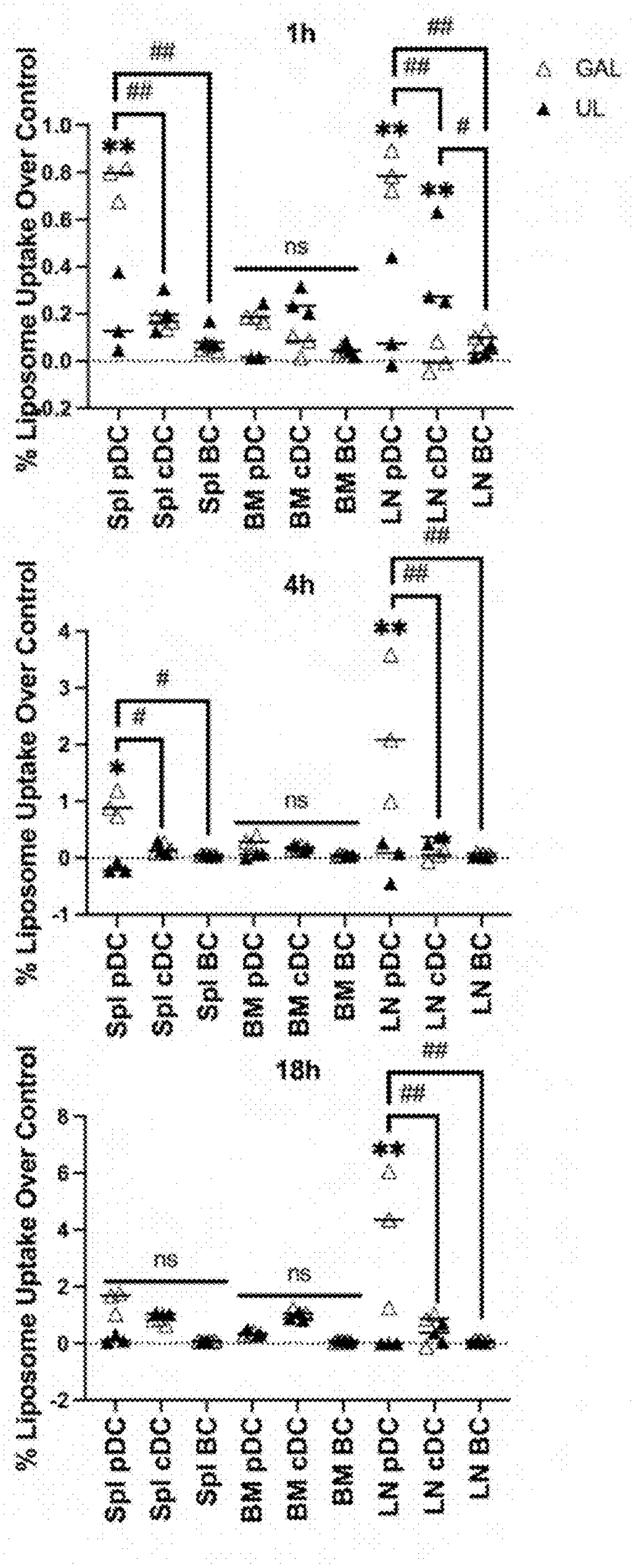
Figure 8C:
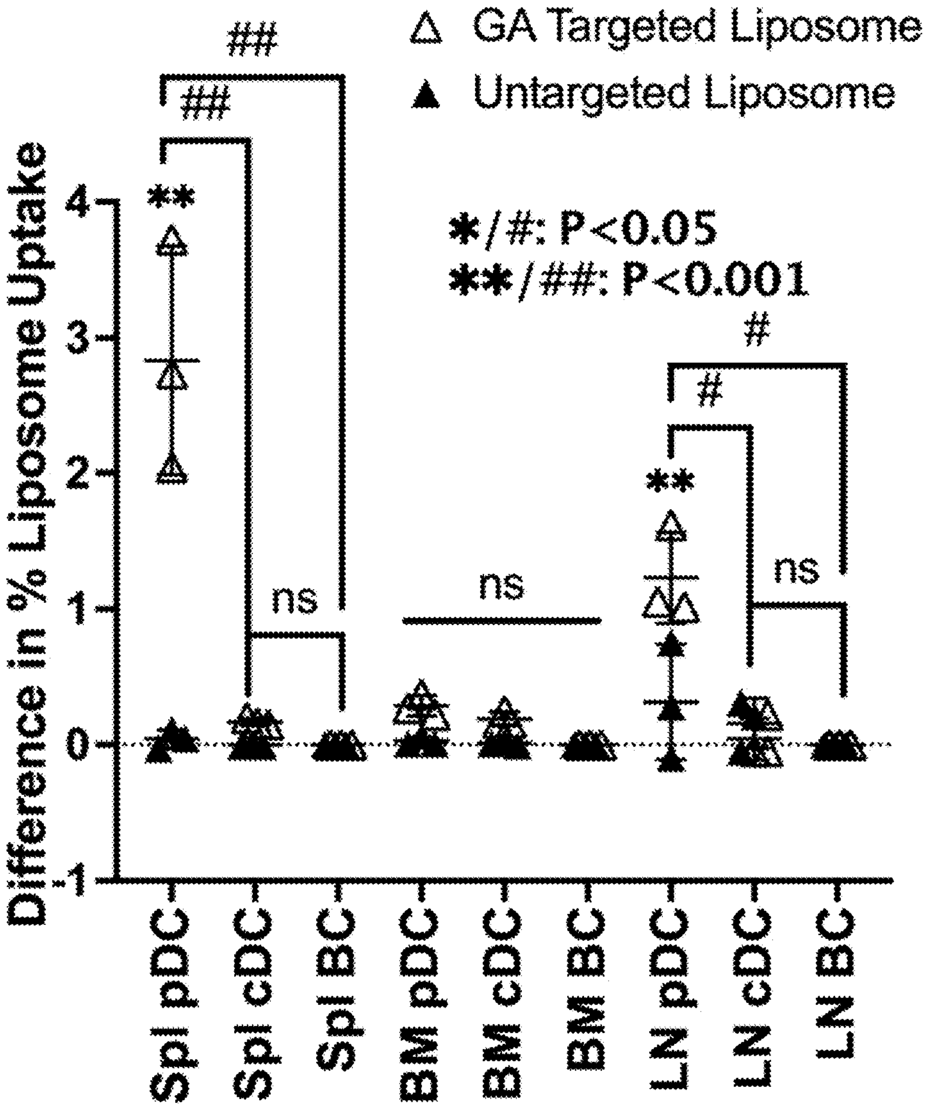

FIG. 8A-8C show GA functionalized liposomes are selectively taken up by pDCs.

FIG. 8A show % of liposome uptake in various spleen, lymph node and bone marrow cells. FIG. 8B show % of liposome uptake in various spleen, lymph node and bone marrow cells at 1 hour, 4 hours and 18 hours. FIG. 8C shows difference in % liposome uptake in in various spleen, lymph node and bone marrow cells. *$p<0.01$, **$p<0.001$, compared with untargeted liposomes, using two-way ANOVA.

Figure 9A:
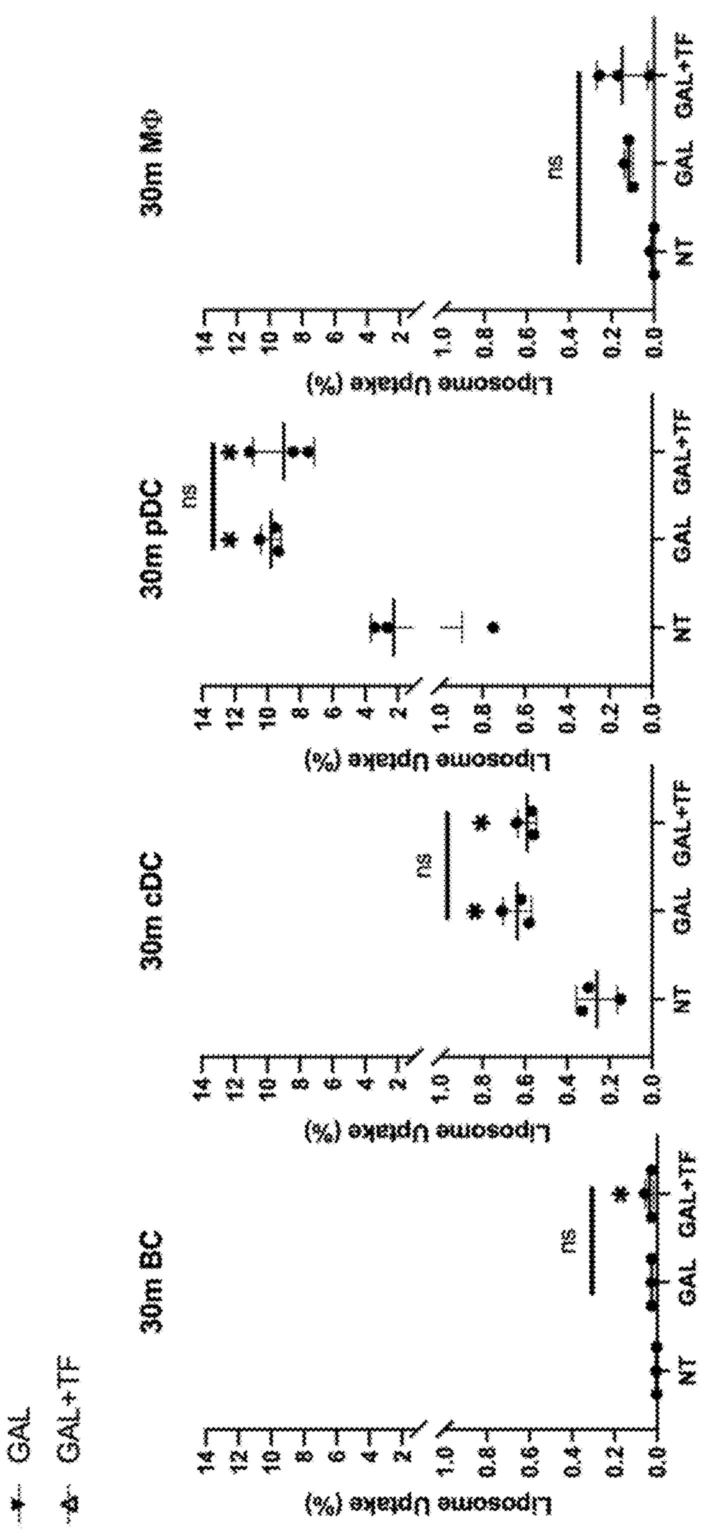
Figure 9B:
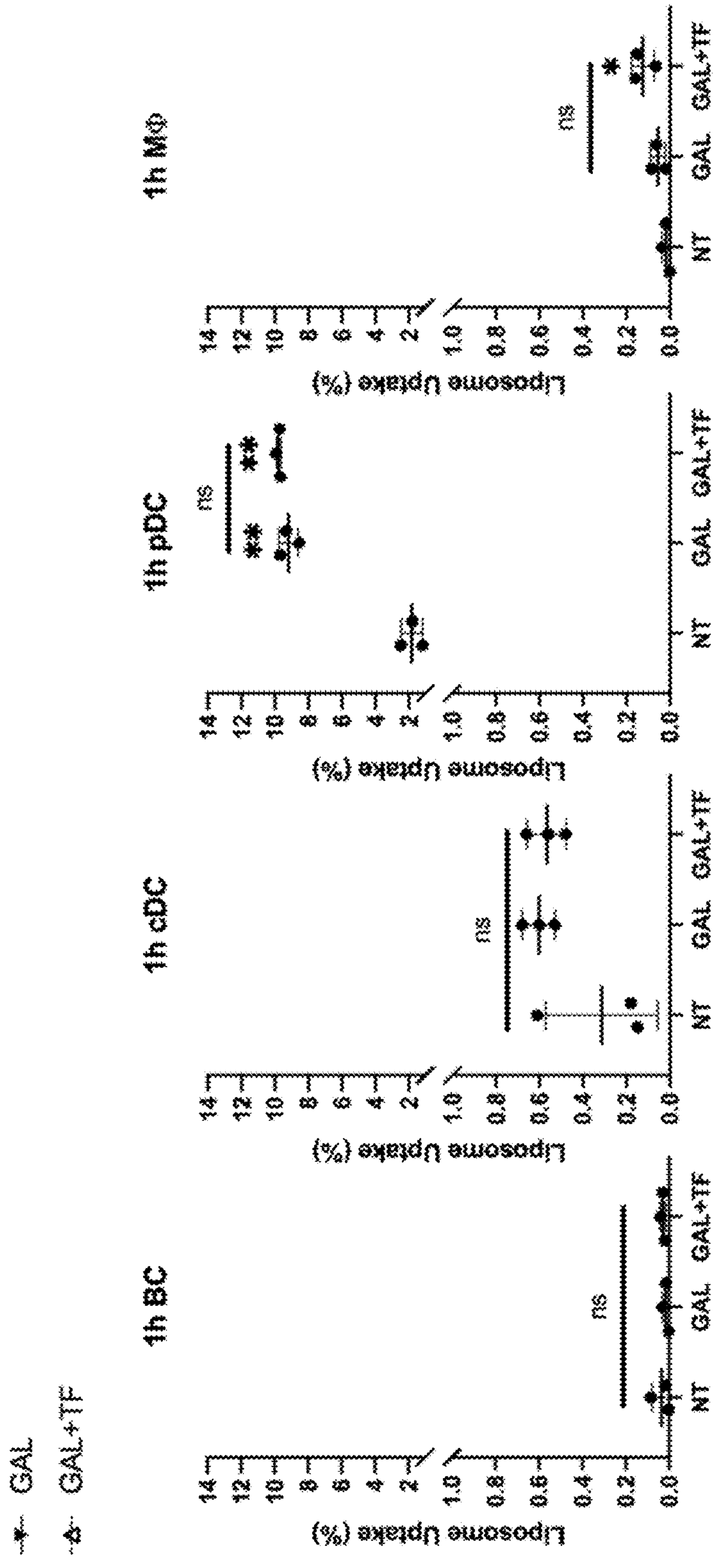
Figure 9C:
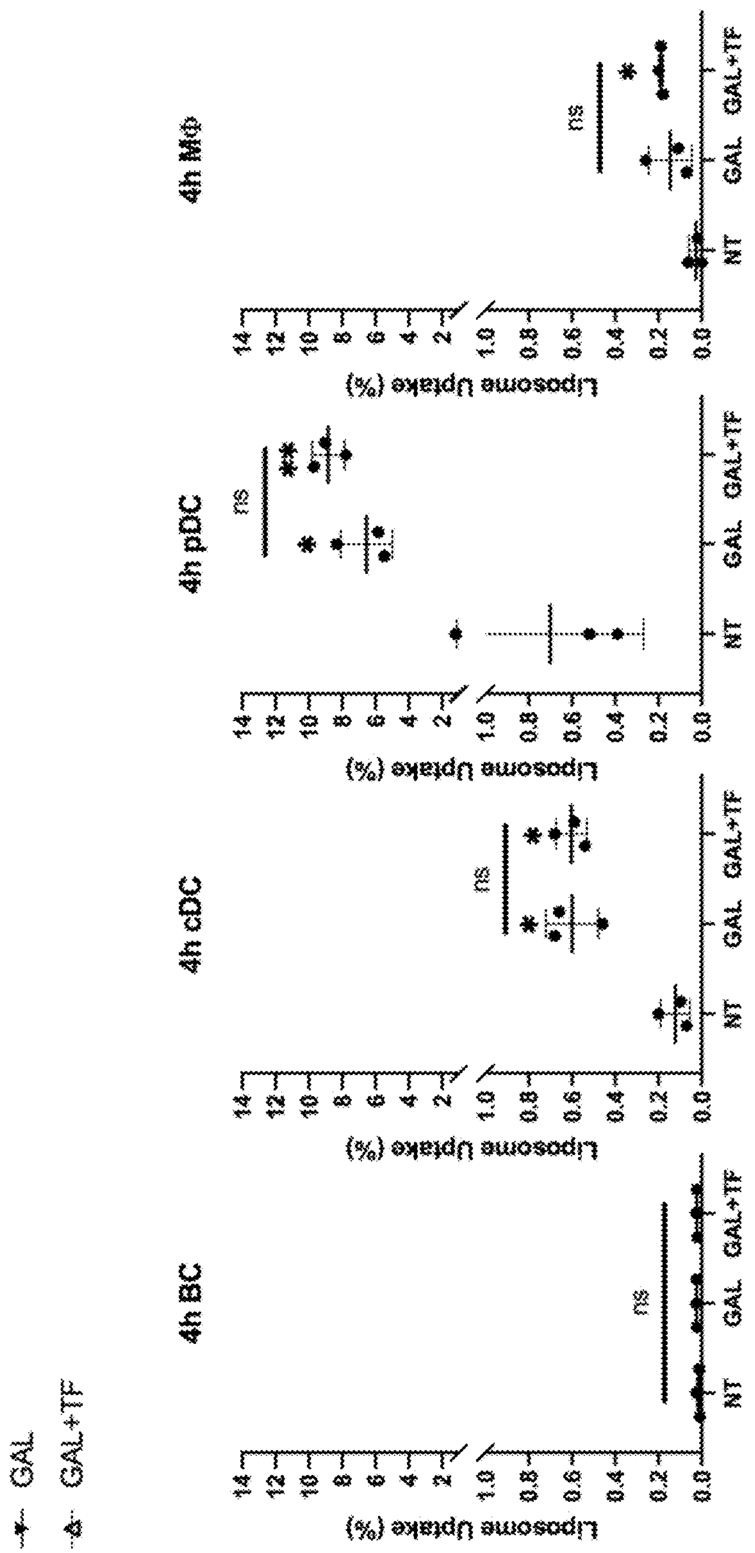
Figure 9D:
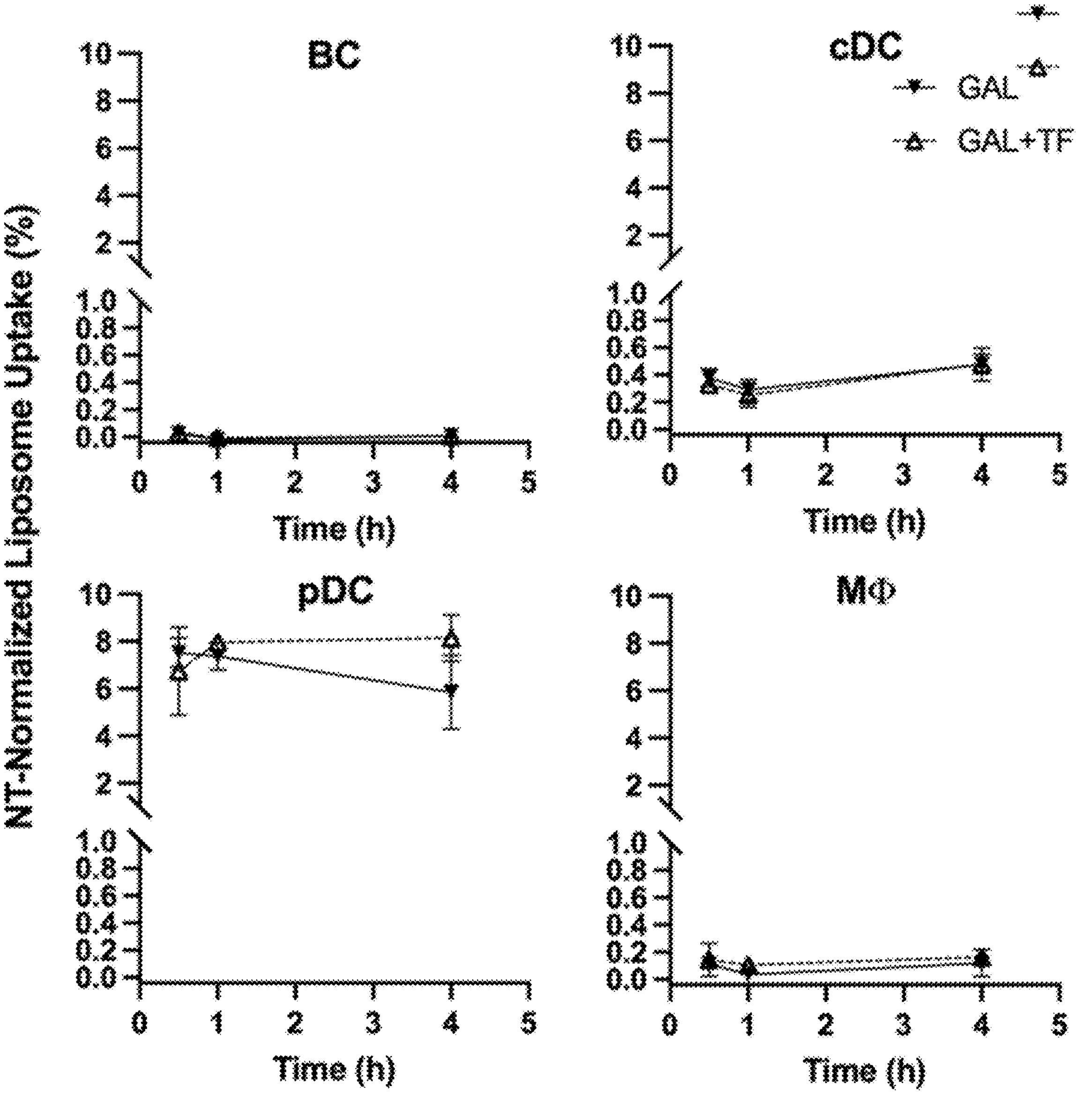
Figure 9E:
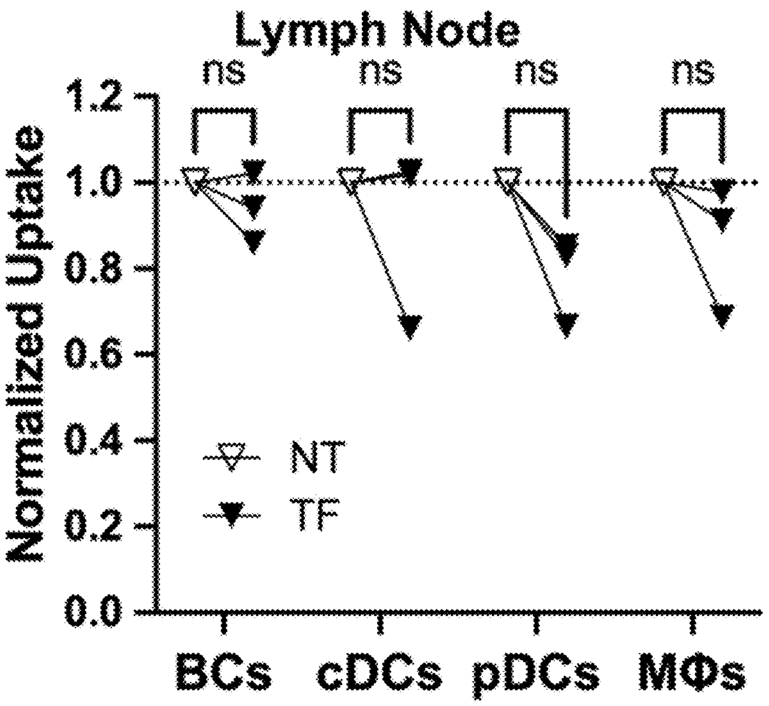
Figure 9F:
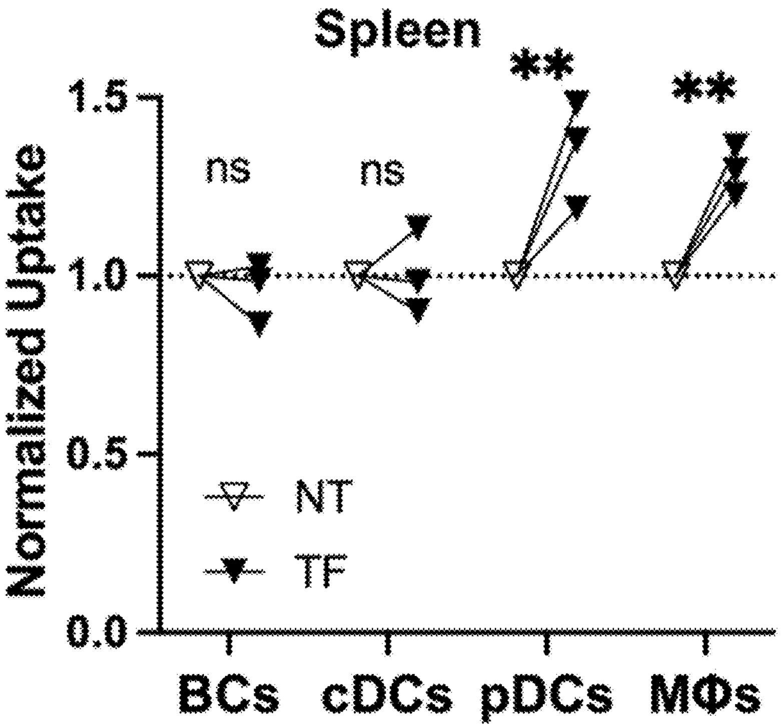

FIG. 9A-9F show that uptake of GA functionalized liposomes is largely noncompetitive with transferrin. FIG. 9A shows % uptake of liposomes at 30 minutes in the presence and absence of transferrin. *$p<0.01$, compared with cells not treated with transferrin, using two-way ANOVA. FIG. 9B shows % uptake of liposomes at 1 hour in the presence and absence of transferrin. $p<0.001$, compared with cells not treated with transferrin, using two-way ANOVA. FIG. 9**C shows % uptake of liposomes at 4 hour in the presence and absence of transferrin. *$p<0.01$, $p<0.001$, compared with cells not treated with transferrin, using two-way ANOVA. FIG. 9D shows normalized uptake of liposomes over time in the presence and absence of transferrin. FIG. 9E shows normalized uptake of liposomes in cells from lymph node in the presence and absence of transferrin. FIG. 9F shows normalized uptake of liposomes in cells from spleen in the presence and absence of transferrin. $p<0.001$, compared with cells not treated with transferrin, using two-way ANOVA.

Figure 10:
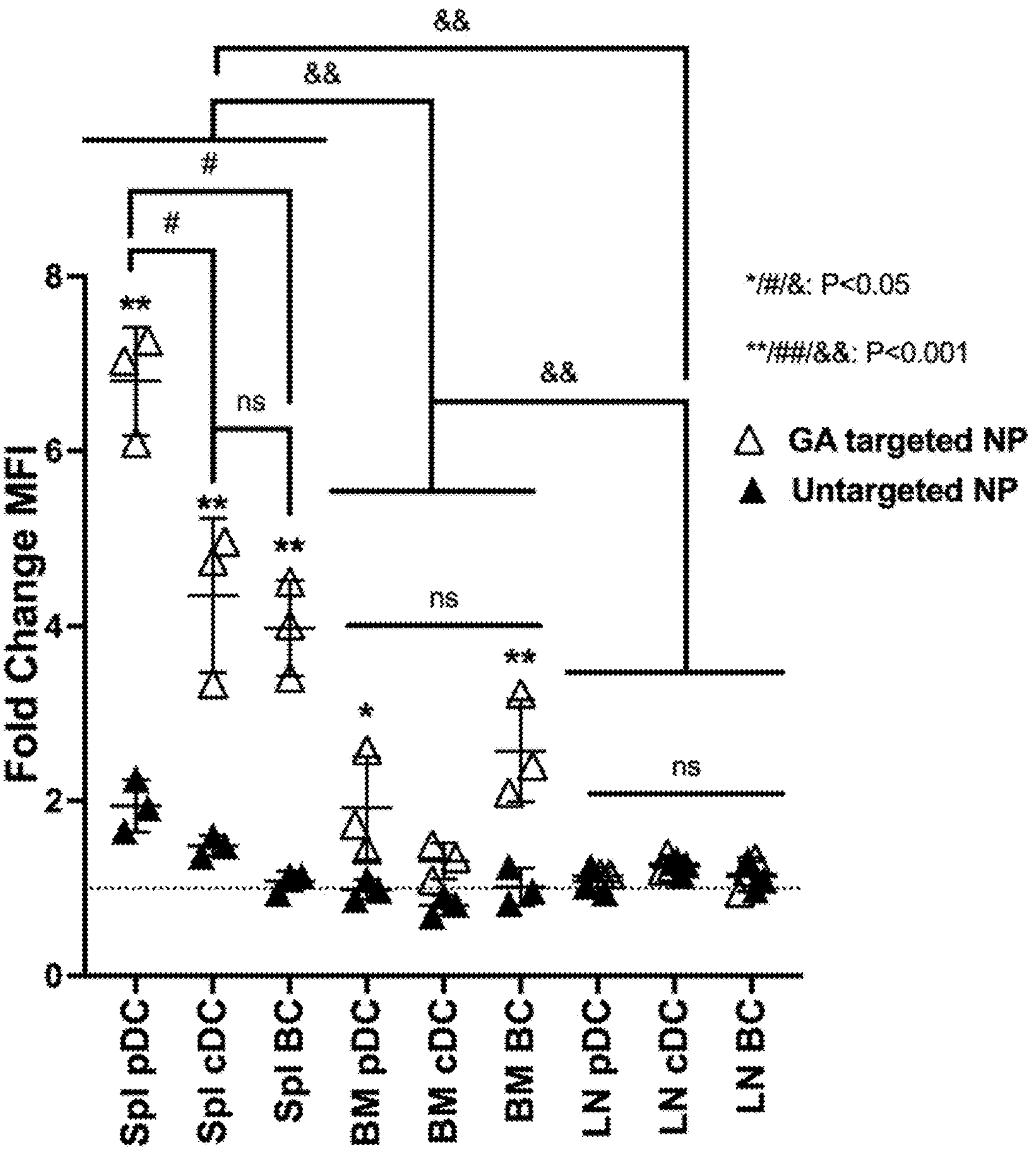

FIG. 10 shows uptake of nanoparticle functionalized with GA in cells in bone marrow (BM), spleen (SPL), and lymph node (LN).

Figure 11:
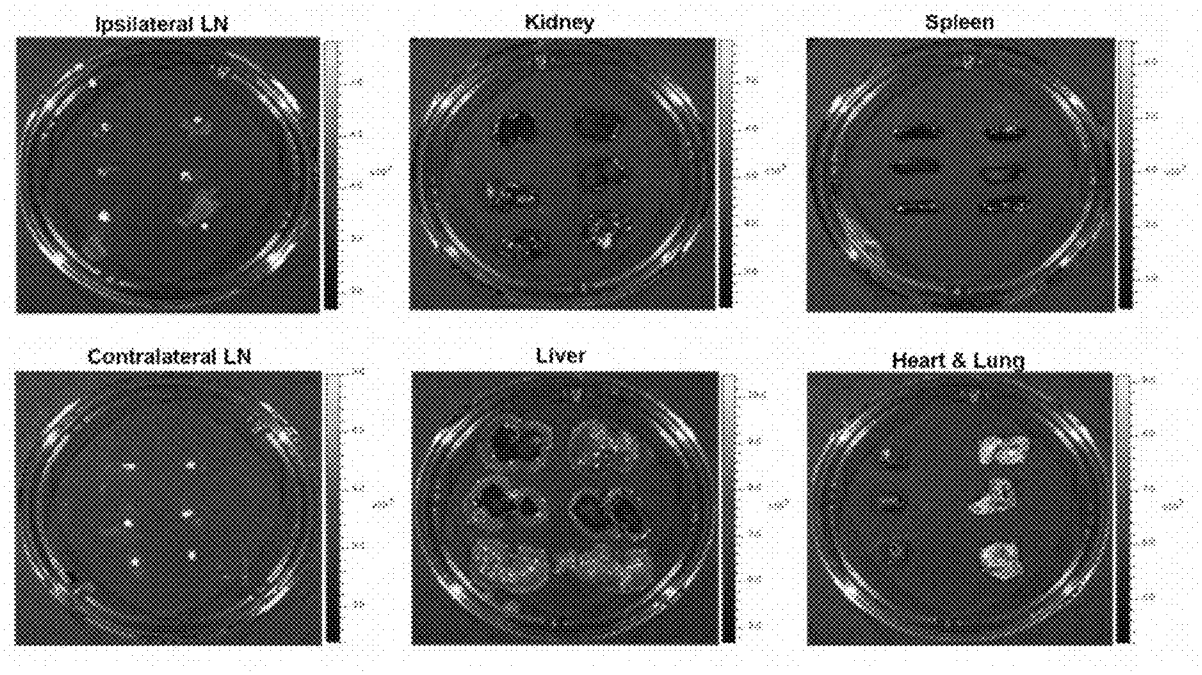

FIG. 11 shows in vivo particle biodistribution 24 hours after footpad injection. Top panel show distribution of GA functionalized liposomes, middle panel show distribution of control liposomes, and bottom panel show distribution of PBS sham.

VI. DETAILED DESCRIPTION

The present disclosure describes a non-competitive active transport strategy using gambogic acid (GA), a small molecule allosteric ligand of CD71, expressed on plasmacytoid dendritic cells (pDCs). The inventors have uniquely identified and optimized a non-viral method of targeted delivery to pDC using a delivery system (for e.g., liposome, nanoparticle) presenting GA. The delivery system described herein can selectively target pDCs for delivery of a cargo (for. eg., a vaccine). The inventors have surprisingly discovered that the disclosed delivery system has enhanced uptake in pDCs and has highly robust mechanism of targeting pDCs.

It is to be understood that the inventive concepts are not limited to specific methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention.

A. Terminology

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

This disclosure describes inventive concepts with reference to specific examples. However, the intent is to cover all modifications, equivalents, and alternatives of the inventive concepts that are consistent with this disclosure.

As used in the specification and the appended claims, the singular forms “a”, “an”, and “the” include plural referents unless the context clearly dictates otherwise.

The phrase ‘consisting essentially of’ limits the scope of a claim to the recited components in a composition or the recited steps in a method as well as those that do not materially affect the basic and novel characteristic or characteristics of the claimed composition or claimed method. The phrase ‘consisting of’ excludes any component, step, or element that is not recited in the claim. The phrase ‘comprising’ is synonymous with ‘including’, ‘containing’, or ‘characterized by’, and is inclusive or open-ended. ‘Comprising’ does not exclude additional, unrecited components or steps.

As used herein, when referring to any numerical value, the term ‘about’ means a value falling within a range that is ±10% of the stated value.

Ranges can be expressed herein as from ‘about’ one particular value, and/or to ‘about’ another particular value. When such a range is expressed, a further aspect includes from the one particular value and/or to the other particular value. Similarly, when values are expressed as approximations, by use of the antecedent ‘about,’ it will be understood that the particular value forms a further aspect. It will be further understood that the endpoints of each of the ranges are significant both in relation to the other endpoint and independently of the other endpoint. It is also understood that there are a number of values disclosed herein, and that each value is also herein disclosed as ‘about’ that particular value in addition to the value itself. For example, if the value ‘10’ is disclosed, then ‘about 10’ is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight component X and 5 parts by weight component Y, X and Y are present at a weight ratio of 2:5, and are present in such ratio regardless of whether additional components are contained in the compound.

As used herein, the terms 'optional' or 'optionally' means that the subsequently described event or circumstance can or cannot occur, and that the description includes instances where said event or circumstance occurs and instances where it does not. In an aspect, a disclosed method can optionally comprise one or more additional steps, such as, for example, repeating an administering step or altering an administering step.

The present disclosure also contemplates that in some aspects, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

As used herein, the term "nucleic acid" refers to isolated, purified, natural, recombinant, synthetic deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the reference sequence explicitly indicated.

The term "oligonucleotide" as used herein is defined as a molecule comprised of two or more deoxyribonucleotides or ribonucleotides, preferably more than three, and usually more than ten. There is no precise upper limit on the size of an oligonucleotide. However, in general, an oligonucleotide is shorter than about 250 nucleotides, preferably shorter than about 200 nucleotides and more preferably shorter than about 100 nucleotides. The exact size will depend on many factors, which in turn depends on the ultimate function or use of the oligonucleotide. The oligonucleotide may be generated in any manner, including chemical synthesis, DNA replication, reverse transcription, or a combination thereof.

As used herein "Lipid" refers to a generic term encompassing fats, lipids, alcohol-ethersoluble constituents of protoplasm, which are insoluble in water. Lipids are composed of fats, fatty oils, essential oils, waxes, steroid, sterols, phospholipids, glycolipids, sulpholipids, aminolipids, chromolipids, and fatty acids. The term encompasses both naturally occurring and synthetic lipids. Preferred lipids in connection with the present invention are: steroids and sterol, particularly cholesterol, phospholipids, including phosphatidyl and phosphatidylcholines and phosphatidylethanolamines, and sphingomyelins. Where there are fatty acids, they could be about 12-24 carbon chains in length, containing up to 6 double bonds. The fatty acids are linked to the backbone, which may be derived from glycerol. The fatty acids within one lipid can be different (asymmetric), or there may be only 1 fatty acid chain present, e.g., lysolecithins. Mixed formulations are also possible, particularly when the non-cationic lipids are derived from natural sources, such as lecithins (phosphatidylcholines) purified from egg yolk, bovine heart, brain, or liver, or soybean.

Lipid particles used herein may be liposomes, lipid complexes, solid lipid nanoparticles, lipoplexes, niosomes, micelles or mixed micelles, oligo- or multilamellar vesicles. Preferably, the lipid particles are liposomes. It is the most preferred embodiment of the invention that the liposomes are cationic liposomes. The method might also employ particles formed through the association of amphiphilic molecules such as detergents. In contrast to liposomes, these structures are based on monolayers which are less stable and tend to disassemble upon dilution.

As used herein, the term "liposome" are lipid vesicles of closed bilayers entrapping an aqueous volume. Liposomes may be unilamellar vesicles, constituted by a single bilayers membrane, or multilamellar vesicles (MLV), constituted by multiple concentric bilayers. Depending on their size, unilamellar vesicles are roughly classified into small unilamellar liposomes (SUV) with an particle size between about 25-100 nm and large unilamellar liposomes (LUV) with an particle size between about 100 nm-10 μm. Hydrophobic drugs are formulated in liposomes by the integration of the drug into the lipid bilayers. Hydrophilic agent may be formulated in liposomes by encapsulation in the aqueous core of the liposomes. Liposomes are capable of influencing pharmacokinetics by a sustained release of the drug to the body or reduce side effects by limiting the free concentration of a drug. By attaching ligands to the liposome or rendering their charge, liposomes facilitate a targeted delivery of drugs to a desired site of action.

As used herein "nanoparticle" or "ultrafine particle" is defined as a particle of matter that is between 1 and 100 nanometers (nm) in diameter. Nanoparticles are small particles, e.g. clusters of metal or semiconductor atoms. The term is also applied for larger particles, up to 500 nm, or fibers and tubes that are less than 100 nm in only two directions. Nanoparticles can occur in a variety of shapes, including as nanospheres, nanorods, nanochains, nanostars, nanoflowers, nanoreefs, nanowhiskers, nanofibers, and nanoboxes. In certain aspects, the nanoparticles and/or nanoparticle cores contemplated herein have a generally polyhedral or spherical geometry. References to "diameter" of a nanoparticle or a nanoparticle core a generally taken to mean the longest dimension of the nanoparticle or nanoparticle core, respectively. As used herein, "corona" refers to a layer or coating, which may partially or completely cover the exposed surface of the nanoparticle core. The corona includes a plurality of ligands covalently attached to the core of the nanoparticle. Thus, the corona may be considered to be an organic layer that surrounds or partially surrounds the metallic core. In certain aspects, the corona provides and/or participates in passivating the core of the nanoparticle. Thus, in certain cases the corona may include a sufficiently complete coating layer substantially to stabilize the core. In certain cases the corona facilitates solubility, such as water solubility, of the nanoparticles.

As used herein, "targeting moiety" or "targeting agent" are intended to mean any agent, such as a functional group, that serves to target or direct the delivery system (e.g., liposome or nanoparticle) to a particular location or association (e.g., a specific binding event). Thus, for example, a targeting moiety may be used to target a delivery system to a specific target protein or enzyme, or to a particular cellular location, or to a particular cell type, to selectively enhance accumulation of the delivery system.

As used herein "Dendritic cells" or "DCs" refers to antigen presenting cells that inform the fight against invasive pathogens while enforcing tolerance to self and harmless environmental antigens. They capture pathogens and receive signals from pathogens that influence the outcome of immune responses. DCs are bone marrow (BM)-derived leukocytes and are the most potent type of antigen-presenting cells. They can also be propagated in vitro from BM and blood using various combinations of growth factors, such as granulocyte macrophage-colony stimulating factor (GM-CSF) and Flt3 ligand. DCs are specialized to capture and process antigens, converting proteins to peptides that are presented on major histocompatibility complex (MHC) molecules recognized by T cells. DCs are heterogeneous, e.g. myeloid and plasmacytoid DCs; although all DCs are capable of antigen uptake, processing and presentation to naive T cells, the DC subtypes have distinct markers and differ in location, migratory pathways, detailed immunological function and dependence on infections or inflammatory stimuli for their generation. During the development of an adaptive immune response, the phenotype and function of DCs play an extremely important role in initiating tolerance, memory, and polarised T-helper 1 (Th1), Th2 and Th17 differentiation. DCs compose approximately 0.1% of monocytes.

As used herein "Plasmacytoid dendritic cells" or "pDCs" are a subset of dendritic cells specialized in secreting high levels of type I interferons. pDCs play a crucial role in antiviral immunity and have been implicated in the initiation and development of many autoimmune and inflammatory diseases. pDCs are generated from hematopoietic stem cells in the bone marrow (BM) via both myeloid and lymphoid precursors. pDCs constitute 0.1-0.5% of human peripheral blood mononuclear cells (PBMCs). Purified pDCs exhibit a plasmacytoid morphology, with rough endoplasmic reticulum and Golgi apparatus. Upon activation, pDCs gain dendritic cell-like morphology and produce massive amounts of type I interferons (IFN-1). Recognition of either pathogen-derived nucleic acids or synthetic TLR ligands such as CpG ODNs initiates IFN-1 secretion by pDCs. The IFN-1 secretion by pDCs is mainly mediated through the activation of the endosomal Toll-like receptors (TLRs) TLR7 and TLR9, with cytosolic receptor initiating pathways playing an important supplementary role. 5 Apart from IFN-I, pDCs could also secrete pro-inflammatory cytokines and chemokines and express co-stimulatory or co-inhibitory molecules which facilitate pDCs to cross-prime CD8+ T cells and present antigens to CD4+ T cells. pDCs produce large quantities of IFNα in response to stimuli (for e.g., viral stimuli). Further, pDCs express CD71 highly and homogenously As used herein "Type I interferons" or "IFN-I" are polypeptides that are secreted by infected cells and induce cell-intrinsic antimicrobial states in infected and neighboring cells that limit the spread of infectious agents, particularly viral pathogens. Type I IFNs are a family of cytokines that all signal through an ubiquitously expressed heterodimeric receptor (IFNAR) resulting in antiviral, antiproliferative and immunomodulatory effects. In humans, type I IFN is composed of at least 12 IFNα protein subtypes and 1 subtype each for IFNβ, IFNε, IFNκ, and IFNω.

As used herein "Interferon α" or "IFNα" are polypeptides which produced in, for example, human leukocyte cells after exposure to viruses or double-stranded RNA, or in transformed leukocyte cell lines (e.g., lymphoblastoid lines). Most IFN-αs are non-glycosylated polypeptides of 165 or 166 amino acids, encoded for by a multigene family of at least 20 genes. The difference in length is due to an amino acid deletion at the $44^{th}$ position in certain IFNs, for instance IFN-α2c. Each gene (termed IFNA1, IFNA2, etc.) encodes a single IFN-α polypeptide subtype (termed IFN-α1, IFN-α2, etc., respectively). Amino acid sequence identity among IFN-α subtypes is generally 80-85% (Horisberger and Di Marco 1995). Within each subtype, individual sequence variants (IFN species) are further denoted with an additional letter designation, e.g., IFN-α2a, IFN-α2b, and IFN-α2c. The sequence differences between these species are often very small (1-3 amino acids).

As used herein "Cluster of Differentiation 71" or "CD71" or "Transferrin receptor protein 1" or "TfR1" refers is a type II glycoprotein which exists as an homodimer, linked by a disulfide bond at position Cys89. This glycoprotein is acylated at Cystein 62 and phosphorylated at Serine 24 by protein kinase C. It contains an internalization signal constituted by a tetrapeptide YTRF (amino acids 20-23). Upon cleavage between Arg 100 and Leu 101 by a yet unknown protease, CD71 becomes soluble. O-glycosylation at Thr 104 reduces the sensitivity of CD71 to cleavage. A ligand of CD71 is the transferrin, protein responsible for iron transport. Recently, it has been shown that CD71 is also a receptor for IgA. Ferrotransferrin binds to CD71 under neutral pH and is internalized in the endosomal compartment. CD71 µlays an essential role in cell proliferation by controlling iron uptake which is essential in several metabolic pathways. This occurs via the binding and the endocytosis of transferrin. Expression of CD71 is post-transcriptionally regulated through RNA stability, it also depends on iron intracellular levels. pDC have been identified to express CD71.

As used herein "Gambogic acid" or "GA" is a xanthonoid isolated from the exudate of Garcinia hanburyi Hook *F.* (*clusiaceae*). Gambogic acid (GA) has the following structure:

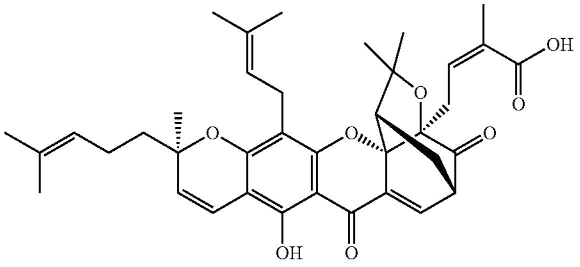 [SMILES: CC(C)=CCC[C@]1(C)C=Cc2c(O)c3c(c(CC=C(C)C)c2O1)O[C@]12C(=C[C@@H]4C[C@H]1C(C)(C)O[C@@]2(C/C=C(/C)C(=O)O)C4=O)C3=O]

As used herein, "expression" refers to the process by which nucleic acid, e.g., DNA, is transcribed into mRNA and translated into peptides, polypeptides, or proteins. If the nucleic acid is derived from genomic DNA, expression may, if an appropriate eukaryotic host cell or organism is selected, include splicing of the mRNA.

As used herein, "transformation" or "transfection" or "nucleic acid delivery" or "gene delivery" refers to the process by which nucleic acids are introduced into cells. Transfection refers to the taking up of exogenous nucleic acid, by a host cell whether or not any coding sequences are in fact expressed. Methods and compositions of the disclosure are effective for transformation or transfection. Successful transfection is generally recognized by detection of the presence of the heterologous nucleic acid within the transfected cell, such as, for example, any visualization of the heterologous nucleic acid or any indication of the operation of a such nucleic acid within the host cell.

As used herein "Endogenous" with reference to a gene, protein, and/or nucleic acid refers to the natural presence of that gene, protein, and/or nucleic acid in a cell, such as an immune cell.

As used herein "Exogenous" refers to an introduced agent, such as a nucleic acid, gene, or protein, into a cell, for example from an outside source. A nucleic acid introduced into a cell is exogenous even if it encodes a protein which is naturally found in the cell. Such exogenous introduction of a nucleic acid encoding a protein can be used to increase the expression of the protein over the level that would naturally be found in the cell under similar conditions, e.g., without introduction of the exogenous nucleic acid.

As used herein "biologically active molecule" is a molecule that is capable of exerting a biological effect upon administration to an individual. As used herein a biologically active molecule is one which may exert its biological activity i.e., exhibits an effect at any level (biochemical, cellular and/or morphological) within the cell in which it is expressed, on the cell surface, effect the cell's interactions with other cells or biologically active molecules or may be released or secreted from the cell in which it is made and exert its effect on a separate target cell (e.g., hormone, growth factor, soluble receptor, antibody, antibody fragment, anti-angiogenic factor, or cytokine). A biologically active molecule is any agent, such as a virus, protein, peptide, amino acid, lipid, carbohydrate, nucleic acid, nucleotide, drug, pro-drug or other substance that may have an effect on cells whether such effect is harmful, beneficial, or otherwise. In some aspects, nucleic acids can include siRNA, shRNA, antisense molecules, plasmids, vectors, etc.

In an aspect, "therapeutically effective amount" means an amount of a disclosed biologically active molecule that (i) treats the particular disease, condition, or disorder, (ii) attenuates, ameliorates, or eliminates one or more symptoms of the particular disease, condition, or disorder, and/or (iii) delays the onset of one or more symptoms of the particular disease, condition, or disorder described herein. The specific therapeutically effective dose level for any particular patient will depend upon a variety of factors including the disorder being treated and the severity of the disorder; the disclosed biologically active molecule, or any combination thereof employed; the disclosed methods employed; the age, body weight, general health, sex and diet of the patient; the time of administration; the route of administration; the rate of excretion of the disclosed biologically active molecule, or any combination thereof employed; the duration of the treatment; drugs used in combination or coincidental with the disclosed biologically active molecule employed, and other like factors well known in the medical arts.

As used herein "Pharmaceutical composition" means a mixture of substances suitable for administering to an individual that includes a pharmaceutical agent. As used herein a pharmaceutical composition comprises delivery system disclosed herein compounded with suitable pharmaceuticals carriers or excipients.

As used herein "Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication, condition or biochemical indicia associated with a disease.

As used herein, the term "patient", "subject", or "test subject" refers to any organism to which provided delivery system described herein are administered in accordance with the present invention e.g., for experimental, diagnostic, prophylactic, and/or therapeutic purposes. Typical subjects include animals (e.g., mammals such as mice, rats, rabbits, non-human primates, humans, insects, worms etc.). In an aspect, a subject is a human. In some aspects, a subject may be suffering from, and/or susceptible to a disease, disorder, and/or condition. In some aspects, the subject is a human.

As used herein "cancer," "tumor," or "malignancy" may refer to one or more neoplasm or cancer. The neoplasm may be malignant or benign, the cancer may be primary or metastatic, the neoplasm or cancer may be early stage or late stage.

As used herein, treatment of cancer can comprise increased inhibition of cancer progression and/or metastases, inhibition of an increase in tumor volume, a reduction in tumor volume and/or growth, a reduction in tumor growth rate, an eradication or killing of a tumor and/or cancer cell, or any combination thereof. In some aspects, the treatment can also prolong the survival of a subject, improve the prognosis and/or improve the quality of life of the subject.

As used herein "inflammatory disease" or "inflammatory disorder" refers to any disease marked by inflammation, which may be caused by a multitude of inciting events, including radiant, mechanical, chemical, infections, and immunological stimuli.

Unless otherwise defined, all technical terms used herein have the same meaning as commonly understood by one of ordinary skill in the art to which this disclosure belongs.

B. Delivery System

Disclosed herein is a targeted delivery system. In some aspects, the delivery system comprises a lipid particle functionalized with a targeting moiety. In some aspects, the delivery system comprises a liposome or a nanoparticle functionalized with a targeting moiety. In some aspects, the targeting moiety binds to CD71. In some aspects, the targeting moiety binds to CD71 noncompetitively with transferrin. In some aspects, the targeting moiety is Gambogic acid (GA).

Liposomes

In some aspects, disclosed herein is a liposome functionalized with a targeting moiety. In some aspects, a liposome functionalized with a targeting moiety herein comprises a targeting moiety that binds to CD71. In some aspects, a liposome functionalized with a targeting moiety herein comprises a targeting moiety that binds to CD71, binds noncompetitively with transferrin. In some aspects, a liposome functionalized with a targeting moiety herein comprises a targeting moiety GA (GAL).

In some aspects, the liposomes described herein may have different sizes, lamellarity and structure. In some aspects, the liposomes herein have an average diameter of about 50 nm to about 500 nm. In some aspects, the liposomes have a diameter of about 50 nm, about 75 nm, about 100 nm, about 125 nm, about 150 nm, about 175 nm, about 200 nm, about 225 nm, about 250 nm, about 275 nm, about 300 nm, about 325 nm, about 350 nm, about 375 nm, about 400 nm, about 425 nm, about 450 nm, about 475 nm, or about 500 nm. In some aspect, liposome has diameter of about 200 nm. The mean diameter of liposomes can be measured using techniques known in the art such as transmission electron microscopy.

In some aspects, the lipid mixture forming the liposome can be selected to achieve a specified degree of fluidity or rigidity, to control the stability of the liposome in serum and to control the rate of release of the entrapped agent in the liposome.

In some aspects, the liposomes herein comprise a lipid that may be of natural source, semi-synthetic or fully synthetic lipid, and neutral, negatively or positively charged. In some aspects, the synthetic vesicle-forming lipids and naturally-occurring vesicle-forming lipids, include the phospholipids (for e.g., egg phophatidylcholine (EPC), 1-palmitoyl-2-oleoylphosphatidyl choline (POPC), distearoylphosphatidylcholine (DSPC) or hydrogenated soy phosphatidylcholine (HSPC)), such as phosphatidylcholine (PC), phosphatidylinositol (PI), phosphatidylglycerol (PG), dimyristoyl phosphatidylglycerol (DMPG); egg yolk phosphatidylcholine (EPC), 1-palmitoyl-2-oleoylphosphatidyl choline (POPC), distearoylphosphatidylcholine (DSPC), dimyristoyl phosphatidylcholine (DMPC); phosphatidic acid (PA), phosphatidylserine (PS) 1-palmitoyl-2-oleoylphosphatidyl choline (POPC), and the sphingophospholipids such as sphingomyelins (SM) having 12-24 carbon atom acyl or alkyl chains. The above-described lipids and phospholipids whose hydrocarbon chain (acyl/alkyl/alkenyl chains) have varying degrees of saturation can be obtained commercially or prepared according to published methods. Other suitable lipids include in the liposomes are glyceroglycolipids and sphingoglycolipids and sterols (such as cholesterol or plant sterol).

In some aspects, liposomes disclosed herein may comprise neutral, and/or anionic lipids. Non-limiting examples of neutral or anionic lipids may be selected from sterols or lipids such as cholesterol, phospholipids, lysolipids, lysophospholipids, sphingolipids or pegylated lipids with a neutral or negative net charge. In certain aspects, neutral and anionic lipids include: phosphatidylserine, phosphatidylglycerol, phosphatidylinositol (not limited to a specific sugar), fatty acids, sterols, containing a carboxylic acid group for example, cholesterol, 1,2-diacyl-sn-glycero-3-phosphoethanolamines, including, but not limited to, 1,2-dioleylphosphoethanolamine (DOPE), 1,2-dihexadecylphosphoethanolamine (DHPE), 1,2-diacyl-glycero-3-phosphocholines, including, but not limited to 1,2-distearylphosphatidylcholine (DSPC), 1,2-dipalmitylphosphatidylcholine (DPPC), 1,2-dimyristylphosphosphatidylcholine (DMPC), phosphatidylcholine preferably egg PC, soy PC, sphingomyelin, or any combination thereof.

In some aspects, liposomes herein, may comprise cationic lipids (mono and polycationic), where the cationic lipid may be included as a minor component of the lipid composition or as a major or sole component. In such aspects, cationic lipids may have a lipophilic moiety, such as a sterol, an acyl or diacyl chain, and where the lipid has an overall net positive charge. In some aspects, the head group of the lipid may carry the positive charge. Non-limiting examples of monocationic lipids may for use in liposomes described herein include, 1,2-dimyristoyl-3-trimethylammonium propane (DMTAP) 1,2-dioleyloxy-3-(trimethylamino)propane (DOTAP); N-[1-(2,3,-ditetradecyloxy)propyl]-N,N-dimethyl-N-hydroxyethylammonium bromide (DMRIE); N-[1-(2,3,-dioleyloxy)propyl]-N,N-dimethyl-N-hydroxy ethyl-ammonium bromide (DORIE); N-[1-(2,3-dioleyloxy)propyl]-N,N,N-trimethylammonium chloride (DOTMA); 3β[N—(N',N'-dimethylaminoethane)carbamoly]cholesterol (DC-Chol); and dimethyl-dioctadecylammonium (DDAB).

In some aspects, polycationic lipids include a similar lipophilic moiety as with the mono cationic lipids, to which polycationic moiety is attached. Exemplary polycationic moieties include spermine or spermidine (as exemplified by DOSPA and DOSPER), or a peptide, such as polylysine or other polyamine lipids. In some aspects, the neutral lipid (DOPE) can be derivatized with polylysine to form a cationic lipid. polycationic lipids include, without being limited thereto, N-[2-[[2,5-bis[3-aminopropyl)amino]-1-oxopentyl] amino]ethyl]-N,N-dimethyl-2,3-bis[(1-oxo-9-octadecenyl) oxy]-1-propanaminium (DOSPA), and ceramide carbamoyl spermine (CCS).

In some aspects, the liposomes may include a lipid derivatized with a hydrophilic polymer (for e.g., lipopolymers). In some aspects, lipopolymers comprise lipids modified at their head group with a polymer. The attachment of the hydrophilic polymer head group to the lipid region may be a covalent or non-covalent attachment, however, is preferably via the formation of a covalent bond (optionally via a linker). The outermost surface coating of hydrophilic polymer chains is effective to provide a liposome with a long blood circulation lifetime in vivo. In some aspects, the lipopolymer may be introduced into the liposome by adding the lipopolymer to a lipid mixture forming the liposome. The lipopolymer will be incorporated and exposed at the inner and outer leaflets of the liposome bilayer. In some aspects, the lipopolymer may be introduced into the liposome by incorporating the lipopolymers to the external leaflet of the pre-formed liposome either by incubation at temperature above the Tm of the lipopolymer and liposome-forming lipids, or by short term exposure to microwave irradiation. Non-limiting examples of polymers used as lipid modifiers include, polyethylene glycol (PEG), polysialic acid, polylactic (also termed polylactide), polyglycolic acid (also termed polyglycolide), apolylactic-polyglycolic acid, polyvinyl alcohol, polyvinylpyrrolidone, polymethoxazoline, polyethyloxazoline, polyhydroxyethyloxazoline, polyhydroxypropyloxazoline, polyaspartamide, polyhydroxypropyl methacrylamide, polymethacrylamide, polydimethylacrylamide, polyvinylmethylether, polyhydroxyethyl acrylate, derivatized celluloses such as hydroxymethylcellulose or hydroxyethylcellulose. The polymers may be used as homopolymers or as block or random copolymers.

In some aspects, liposomes disclosed herein phosphatidyl ethanolamine (PE). In some aspects, the liposomes disclosed herein comprise distearylphosphatidylethanolamine (DSPE). In some aspects, the disclosed comprise PEG attached to DSPE. In some aspects, the PEG polymer is linked to the lipid via a carbamate linkage. In some aspects, different lengths of PEG chains can be employed. In some aspects, the PEG has a molecular weight of from about 750 Daltons to about 20,000 Daltons. In some aspects, the molecular weight is from about 750 Daltons to about 12,000 Daltons and some aspect between about 1,000 Daltons to about 5,000 Daltons. In some aspects, PEG, has a molecular weight between 500-10,000 Daltons, between 750-10,000 daltons, between 750-5000 daltons. In some aspects, the PEG is Methoxy or ethoxy-capped analogues of PEG. In some aspects, PEG is commercially available PEG in a variety of polymer sizes, e.g., 120-20,000 Daltons. In some aspects, PEG-DSPE employed herein comprise PEG with a molecular weight of 2000 Da.

In some aspects, the PEG chains can be functionalized to comprise reactive groups suitable for coupling with, for example, sulfhydryls, amino groups, and aldehydes or ketones present in a wide variety of ligands. Examples of such PEG-terminal reactive groups include maleimide (for reaction with sulfhydryl groups), N-hydroxysuccinimide (NHS) or NHS-carbonate ester (for reaction with primary amines), hydrazide or hydrazine (for reaction with aldehydes or ketones), iodoacetyl (preferentially reactive with sulfhydryl groups) and dithiopyridine (thiol-reactive).

It will be appreciated that any of the hydrophilic polymers recited above in combination with any of the vesicle-forming lipids recited above can be employed as modifying agents to prepare the lipid-polymer-ligand targeting conjugate and suitable reaction sequences for any selected polymer can be determined by those of skill in the art.

The methods for preparation of liposomes can include thin-film hydration method, ethanol injection method, reverse-phase evaporation method and double emulsion method. In some aspects, the disclosed liposome are prepared using thin-film hydration method. Briefly, thin-film hydration method involves dissolving phospholipids in an organic solvent, making a thin lipid film in a container (for e.g., round-bottom flask) by the removal of organic solvent, by evaporating to dryness. Dispersion medium is added, and the mixture may be optionally heated to above the phase transition temperature, and agitated which results in the formation of heterogeneous liposomes. The method can further comprise extrusion through polycarbonate membranes, to obtain homogeneous liposomes.

In some aspects, liposome are prepared using a continuous method for preparation of liposomes from a starting suspension or solution comprising lipids, and dehydrating said liposomes by spray-drying or spray-freeze-drying, whereby the method comprises extruding a suspension or solution comprising lipids through a porous device and subsequently passing the suspension or solution through a nozzle, whereby the suspension is atomized to form droplets.

In an exemplary aspect, PEG bis amine is reacted with 2-nitrobenzene sulfonyl chloride to generate the monoprotected product. Monoprotected product is reacted with carbonyl diimidazole in triethylamine (TEA) to form the imidazole carbamate of the mono 2-nitrobenzenesulfonamide. Mono 2-nitrobenzenesulfonamide is reacted with DSPE in TEA to form the derivatized PE lipid protected at one end with 2-nitrobenzyl sulfonyl chloride. The protecting group is removed by treatment with acid to give the DSPE-PEG product having a terminal amine on the PEG chain. Reaction with maleic acid anhydride gives the corresponding maleamic product, which on reaction with acetic anhydride gives the desired PE-PEG-maleimide product. The compound is reactive with sulfhydryl groups, for coupling the targeting moieties described herein through a thioether linkage.

In certain aspects, liposome can be functionalized with targeting moiety, GA, by using copper catalyzed azide-alkynecyclo addition between GA-alkyne and DSPE-[PEG2000]-azide as shown in FIG. 4A.

Nanoparticles

In some aspects, disclosed herein is a nanoparticle functionalized with a targeting moiety. In some aspects, a nanoparticle functionalized with a targeting moiety herein comprises a targeting moiety that binds to CD71. In some aspects, a nanoparticle functionalized with a targeting moiety herein comprises a targeting moiety that binds to CD71, binds noncompetitively with transferrin. In some aspects, a nanoparticle functionalized with a targeting moiety herein comprises a targeting moiety GA (GAL).

In some aspects, the nanoparticles herein may have a core, while in other aspects they may not have a core. In some aspects, the nanoparticles herein have cores having mean diameters between about 10 nm and about 100 nm, from about 40 nm to about 75 nm, about 0.5 and about 50 nm, between about 0.5 and about 10 nm, between about 0.5 and about 5 nm, between about 0.5 and about 3 nm and between about 0.5 and about 2.5 nm. When the targeting moieties are considered in addition to the cores, the overall mean diameter of the particles is between about 2.0 and about 50 nm, between about 3 and about 10 nm. In some aspects, the core diameter may be may be from about 50 nm to about 60 nm. In some aspect, the diameter of the core may be about 10 nm, about 15 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, or about 100 nm. The mean diameter can be measured using techniques known in the art such as transmission electron microscopy.

In some aspects, the core material of the nanoparticles herein can be a metal or semiconductor and may be formed of more than one type of atom. In some aspects, the core material of the nanoparticles herein is a metal selected from Au, Fe or Cu. In some aspects, nanoparticle cores may also be formed from alloys including Au/Fe, Au/Cu, Au/Gd, Au/Fe/Cu, Au/Fe/Gd and Au/Fe/Cu/Gd, and may be used in the present disclosure. In some aspects, the cores of the nanoparticles preferably comprise between about 100 and 500 atoms (e.g. gold atoms) to provide core diameters in the nanometre range. In some aspects, the nanoparticles herein designed to have a core, may be made, from materials such as, but not limited to, iron(III) oxide, carbon, carbon nanotubes, cadmium selenide, titanium, titanium dioxide, tin, tin oxide, silicon, silicon dioxide, iron, nickel, silver, copper, aluminum, steel, titanium alloy, brushite, tricalcium phosphate, chitosan, alumina, silica, lipinds, polystyrene, polylactides, silicone rubber, polycarbonate, polyurethane, polypropylene, polymethylmethaacrylate, polyvinyl chloride, polyester, polyether, or polyethylene. In some aspects, the core materials may be doped with one or more atoms that are NMR active, allowing the nanoparticles to be detected using NMR, both in vitro and in vivo. Examples of NMR active atoms include $Mn^{+2}$, $Gd^{+3}$, $Eu^{+2}$, $Cu^{+2}$, $V^{+2}$, $Co^{+2}$, $Ni^{+2}$, $Fe^{+2}$, $Fe^{+3}$ and lanthanides$^{+3}$, or the quantum dots.

In some aspects, nanoparticles formed with a core may also include other structural features. For example, molecules may be associated with the core to facilitate particle dispersion in solution, influence overall particle charge or zeta potential, or to allow the particle to incorporate a cargo, such as a pharmacological agent. Polymeric conjugates provided herein may be useful to improve solubility and/or stability of a bioactive/therapeutic agent, reduce drug-drug interactions, reduce interactions with blood elements including plasma proteins, reduce or eliminate immunogenicity, protect the agent from metabolism, modulate drug-release kinetics, improve circulation time, improve drug half-life (e.g., in the serum, or in selected tissues, such as tumors), attenuate toxicity, improve efficacy, normalize drug metabolism across subjects of different species, ethnicities, and/or races, and/or provide for targeted delivery into specific cells or tissues. Poorly soluble and/or toxic compounds may benefit particularly from incorporation into polymeric compounds of the invention. In some embodiments ore-associated molecules may be chemical polymers. In some aspects, a core particle may be associated, covalently or non-covalently, with a hydrophilic polymer. In some aspects, hydrophilic polymers associated with a core particle may be a polymer or copolymer (block or random) of poly(ethylene glycol), polyvinyl alcohol, polyvinyl acid, poly(meth)acrylate, poly(meth)acrylamide, polylactic acid (PLA), polyglycolic acid (PGA), polycaprolactone (PCL), poly(Lactide-co-Glycolide) (PLGA), collagen, elastin, thrombin, fibronectin, starches, poly(amino acid), poly(propylene fumarate), gelatin, alginate, pectin, fibrin, oxidized cellulose, chitin, chitosan, tropoelastin, hyaluronic acid, polypeptides, proteins, polysaccharides, hyaluronic acid and alginate, acyl-substituted cellulose acetates, polyethylene oxide, glycerin, sorbitol, mannitol, sucrose, sorbitan, glycerol, xylitol, isomalt, polypropylene glycol, and poly(tetramethylene ether)glycol, polycaprolactones or polyester adipate polyols, polyether polyols, trehalose, lactose, glucose, or dextran, as well as biopolymers known in the art, may also be suitable for use in this regard. In some aspects, the nanoparticles herein include a core particle, associated with polyethylene glycol. In some aspects, polyethylene glycol may be covalently bound to a core particle.

In some aspects, the targeting moieties described herein may be associated with the nanoparticle by methods known in the art. For example, in some aspects, targeting moieties may be attached to an nanoparticles via linkage to a core associated polymer, such as polyethylene glycol. In some aspects, more than one targeting moiety can be conjugated or otherwise associated with a nanoparticle, and the target ligand for each targeting moiety can be the same or different.

In some aspects, the targeting ligand may be covalently linked to the nanoparticle core directly or via a linker. In some aspects, GA functionalized nanoparticle comprise poly (lactide-co-glycolide) (PLGA) and can be synthesized by linking GA to the carboxyl end groups of PLGA via an ethylenediamine linker using carbodiimide chemistry. In some aspects, stable nanoparticles can be formed from the PLGA-GA polymer via simple emulsion techniques with a desired size profile (for e.g., 90-150 mm). In some aspects, the carboxy-terminal end group of PLGA can be activated with 1-ethyl-3-(dimethylaminopropyl) carbodiimide (EDC) and connected to n-boc-ethylenediamine via an amide bond, which then can be de-protected to get PLGA-EDA with a free amine group. The amine functionality allow for the formation of an amide-linkage to the carboxyl group of GA in the subsequent reaction.

Targeting Moiety

In some aspects, the disclosure encompasses liposomes or nanoparticles functionalized with a targeting moiety. In some aspects, the targeting moiety binds to a receptor expressed on pDCs. In some aspects, the targeting moiety binds to CD71. In some aspects, the targeting moiety binds to CD71 non-competitively with receptor on pDCs. In some aspects, the targeting moiety binds to CD71 noncompetitively with transferrin.

In some aspects, the disclosed targeting moiety binds to CD71. In some aspects, the targeting moiety is GA. In such aspects, the targeting moiety enhances the delivery of the liposomes to cells expressing CD71. In some aspects, the targeting moiety enhances the delivery of the liposomes or nanoparticles to pDCs.

In some aspects, the targeting moiety enhances the delivery of the liposomes or nanoparticles to pDCs cells. In some aspects, the targeting moiety is GA. In some aspects, the targeting moiety GA enhances the delivery of the liposomes or nanoparticles to pDCs cells by at least by 10% compared to liposomes or nanoparticles without the targeting moiety. In some aspects, the delivery of liposomes or nanoparticles is enhanced by at least about 10%, about 15%, about 20%, about 25%, about 30%, about 35%, about 40%, about 45%, about 50%, about 55%, about 60%, about 65%, about 70%, about 75%, about 80%, about 85%, about 90% or above, to pDCs compared to liposomes or nanoparticles without the targeting moiety. In some aspects, the targeting moiety GA enhances the delivery of the liposomes or nanoparticles to pDCs cells by at least by about 25% compared to liposomes or nanoparticles without the targeting moiety.

In some aspects, the targeting moiety enhances the delivery of the liposomes or nanoparticles to cells expressing CD71. In some aspects, the targeting moiety is GA. In some aspects, the targeting moiety GA enhances the delivery of the liposomes or nanoparticles to cells expressing CD71 by at least by 10% compared to liposomes or nanoparticles without the targeting moiety. In some aspects, the delivery of liposomes or nanoparticles is enhanced by at least about 10%, about 15%, about 20%, about 25%, about 30%, about 35%, about 40%, about 45%, about 50%, about 55%, about 60%, about 65%, about 70%, about 75%, about 80%, about 85%, about 90% or above to CD71, compared to liposomes or nanoparticles without the targeting moiety. In some aspects, the targeting moiety GA enhances the delivery of the liposomes or nanoparticles to cells expressing CD71 by at least by about 25% compared to liposomes or nanoparticles without the targeting moiety.

In some aspects, targeting moiety binds to CD71 non-competitively with a natural ligand of CD71. In some aspects, the targeting moiety is GA, and the natural ligand of CD71 is transferrin. In some aspects, the percentage difference in the delivery of liposomes or nanoparticles to pDCs, in the presence of transferrin is less than about 50% compared to the delivery of liposomes or nanoparticles in the absence of transferrin.

In some aspects, the percentage difference in the delivery of liposomes or nanoparticles to the pDCs, in the presence of transferrin is less than about 10%, about 15%, about 20%, about 25%, about 30%, about 35%, about 40%, about 45%, about 50%, compared to the delivery of liposomes or nanoparticles in the absence of transferrin.

In some aspects, the liposomes, nanoparticles or the targeting moiety may further comprise a detectable label. The label may be an element of the core of the nanoparticle, or an incorporated in the liposome. The label may be detectable because of an intrinsic property of that element of the nanoparticle or by being linked, conjugated or associated with a further moiety that is detectable. Preferred examples of labels include a label which is a fluorescent group, a radionuclide, a magnetic label or a dye. Fluorescent groups include fluorescein, rhodamines or tetramethyl rhodamine, Texas-Red, Cy3, Cy5, etc., and may be detected by excitation of the fluorescent label and/or detection of the emitted light using Raman scattering spectroscopy.

In some aspects, the liposomes, nanoparticles or the targeting moiety may comprise a radionuclide for use in detecting the liposomes, nanoparticles or the targeting moiety using the radioactivity emitted by the radionuclide, e.g. by using PET, SPECT, or for therapy, (e.g., for killing target cells). Non-limiting examples of radionuclides include 99mTc, which exists in a variety of oxidation states although the most stable is TcO4-; 32P or 33P; 57Co; 59Fe; 67Cu which is often used as Cu2+ salts; 67Ga which is commonly used a Ga3+ salt, e.g. gallium citrate; 68Ge; 82Sr; Mo; 103Pd; mln which is generally used as In3+ salts; 125I or 1311 which is generally used as sodium iodide; 137Cs; 153Gd; 153Sm; 158Au; 186Re; 201T1 generally used as a T1+ salt such as thallium chloride; $39Y^{3+}$; $7iLu^{3+}$; anci 24Cr2+ The general use of radionuclides as labels and tracers is well known in the art and could readily be adapted by the skilled person for use in the aspects of the present invention. The radionuclides may be employed most easily by doping the cores of the nanoparticles or including them as labels present as part of targeting moiety functionalized on the liposomes or nanoparticles.

Cargo

In further aspects, the liposomes, or the nanoparticles herein may comprise a cargo comprising a therapeutic agent or a biologically active agent. In some aspects, the therapeutic agent or the biologically active agent is a nucleic acid, an antiviral agent, an antibacterial agent, an antifungal agent, an antimetabolic agent, an anticancer agent, anti-inflammatory agent, a polypeptide, a protein, or a diagnostic agent.

In some aspects, the nucleic acids comprise DNA, cDNA, RNA, iRNA, siRNA, miRNA, shRNA, antisense oligonucleotides (ASO) or other oligonucleotides. Nucleic acid in any form and from any natural, synthetic or recombinant source, including, but not limited to dsDNA, ssDNA, ssRNA, DNA-RNA duplex, Cas9-guideRNA complex, oligonucleotides, nucleotides or nucleotide analogs may be used in the delivery system disclosed herein. In some aspects, the nucleic acid disclosed herein may serve as antisense, competitive agents for binding DNA binding proteins, expression constructs for expressing a protein product, regulatory sequences, and the like. In some aspects, the nucleic acid disclosed herein may be used for down-regulation or silencing genes. For example, expressed protein activity can be down-regulated or eliminated using antisense oligonucleotides (ASOs), nucleotide aptamers, and RNA interference (RNAi) (e.g., small interfering RNAs (siRNA), short hairpin RNA (shRNA), and micro RNAs (miRNA). Any method available in the art for the preparation, isolation, synthesis, or purification of such nucleic acid, may be used.

In some aspects, antiviral agent encompasses any agent or a vaccine that may be used for treating, preventing, or reducing the occurrence of viral infection including infection caused by herpesviruses such as herpes simplex virus type 1 (HSV-1), herpes simplex virus type 2 (HSV-2), varicella-zoster virus (VZV) and cytomegalovirus (CMV), viruses belonging to the family Orthomyxoviridae such as viruses belonging to the family (collectively referred to as herpes viruses), influenza A viruses, influenza B viruses, influenza C viruses (collectively referred to as influenza viruses), human immunodeficiency Viruses belonging to retroviridae such as virus (HIV), viruses belonging to paramyxoviridae such as measles virus and mumps virus, viruses belonging to picornaviridae such as poliovirus, rhinovirus and hepatitis A virus, type B Viruses belonging to the family Hepadnaviridae such as flame virus, viruses belonging to Flaviviridae such as hepatitis C virus, Japanese encephalitis virus and West Nile virus, viruses belonging to the adenoviridae family such as human adenovirus, coronavirus, SARS virus, viruses belonging to the Coronaviridae family such as COVID19, viruses belonging to the Togaviridae family such as rubella virus, viruses belonging to the Rhabdoviridae family such as rabies virus and vesicular stomatitis virus, viruses belonging to the Filoviridae family such as Ebola virus, and human papillomaviruses, viruses belonging to the family of papovaviridae such as (HPV).

In some aspects, antibacterial agent encompasses any agent that may be used for treating, preventing, or reducing the occurrence of bacterial infection including infection caused by *Moraxella* spp., Costridium spp., *Corynebacterium* spp., Diplococcus spp., *Flavobacterium* spp., Hemophilus spp., *Klebsiella* spp., Leptospira spp., *Mycobacterium* spp., *Neisseria* spp., *Propionibacterium* spp., *Proteus* spp., *Pseudomonas* spp., *Serratia* spp., *Escherichia* spp., *Staphylococcus* spp., *Streptococcus* spp., and bacteria-like organisms including *Mycoplasma* spp. and *Rickettsia* spp. In some aspects, the antibacterial agent may be an antibiotic, non-limiting examples of which include penicillin, ampicillin, netacillin, carbencillin, tetracycline, tetracycline hydrochloride, oxtetracycline hydrochloride, chlortetracycline hydrochloride, 7-chloro-6-dimethyltetracycline, doxycycline, doxycycline monohydrate, methacycline hydrochloride, minocycline hydrochloride, rolitetracycline, dihydrostreptomycin, streptomycin, gentamicin, kanamycin, neomycin, erythromycin, carbomycin, oleandomycin, troleandomycin, Polymysin B, collistin, cephalothin sodium, cephaloridine, cephaloglycin dehydrate, cephalexin monohydrate, or any combination thereof.

In some aspects, antifungal agent encompasses any agent that may be used for treating, preventing, or reducing the occurrence of fungal infection including infection caused by any pathogenic or opportunistic fungi, including those from the genera *Candida, Aspergillus, Cryptococcus, Histoplasma, Pneumocystis, Coccidioides* Mycetoma, *Paracoccidioides*, and Stachybotrys, each of which is among prominent fungal pathogens. Species such as *C. albicans, Aspergillus fumigatus, Aspergillus clavatus, Cryptococcus neoformans, Cryptococcus laurentii, Cryptococcus albidus, Cryptococcus gattii, Histoplasma capsulatum, Pneumocystis carinii*, or Stachybotrys chartarum. In some aspects, the antifungal agent may be an anti-fungal drug non-limiting example of which include Amphotericin B, Candicidin, Filipin, Hamycin, Natamycin, Nystatin, Rimocidin, Bifonazole, Butoconazole, Clotrimazole, Econazole, Fenticonazole, Isoconazole, Ketoconazole, Miconazole, Omoconazole, Oxiconazole, Sertaconazole, Sulconazole, Tioconazole, Albaconazole, Fluconazole, Isavuconazole, Itraconazole, Posaconazole, Ravuconazole, Terconazole, Voriconazole, Abafungin, Amorolfin, Butenafine, Naftifine, Terbinafine, Anidulafungin, Caspofungin, Micafungin, Ciclopirox, Flucytosine, Griseofulvin, Haloprogin, Polygodial, Tolnaftate, Undecylenic acid, or any combination thereof.

In some aspects, an anticancer agent herein may be herbal drugs, chemotherapeutic agents, or any combination thereof. In further aspects, the anticancer drug may be Epigallocatechin-3-gallate (EGCG), soy isoflavones, Isoflavones genistein, daidzein, Coumarins, flavonoids, silibinin, polyphenols, baicalin, lycopenes, 5-fluorouracil, actinomycin D, Abarelix, Abciximab, Aclarubicin, Adapalene, Alemtuzumab, Altretamine, Aminoglutethimide, Amiprilose, Amrubicin, Anastrozole, Ancitabine, Artemisinin, Azathioprine, Basiliximab, Bendamustine, Bevacizumab, Bexxar, Bicalutamide, Bleomycin, Bortezomib, Broxuridine, Busulfan, Campath, Capecitabine, Carboplatin, Carboquone, Carmustine, Cetrorelix, Chlorambucil, Chlormethine, Cisplatin, Cladribine, Clomifene, Cyclophosphamide, Dacarbazine, Daclizumab, Dactinomycin, Dasatinib, Daunorubicin, Decitabine, Deslorelin, Dexrazoxane, Docetaxel, Doxifluridine, Doxorubicin, Droloxifene, Drostanolone, Edelfosine, Eflornithine, Emitefur, Epirubicin, Epitiostanol, Eptaplatin, Erbitux, Erlotinib, Estramustine, Etoposide, Exemestane, Fadrozole, Finasteride, Floxuridine, Flucytosine, Fludarabine, Fluorouracil, Flutamide, Formestane, Foscarnet, Fosfestrol, Fotemustine, Fulvestrant, Gefitinib, Genasense, Gemcitabine, Glivec, Goserelin, Gusperimus, Herceptin, Idarubicin, Idoxuridine, Ifosfamide, Imatinib, Improsulfan, Infliximab, Irinotecan, Ixabepilone, Lanreotide, Lapatinib, Letrozole, Leuprorelin, Lobaplatin, Lomustine, Luprolide, Melphalan, Mercaptopurine, Methotrexate, Meturedepa, Miboplatin, Mifepristone, Miltefosine, Mirimostim, Mitoguazone, Mitolactol, Mitomycin, Mitoxantrone, Mizoribine, Motexafin, Mylotarg, Nartograstim, Nebazumab, Nedaplatin, Nilutamide, Nimustine, Octreotide, Ormeloxifene, Oxaliplatin, Paclitaxel, Palivizumab, Panitumumab, Patupilone, Pazopanib, Pegaspargase, Pegfilgrastim, Pemetrexed, Pentetreotide, Pentostatin, Perfosfamide, Piposulfan, Pirarubicin, Plicamycin, Prednimustine, Procarbazine, Propagermanium, Prospidium Chloride, Raloxifen, Raltitrexed, Ranimustine, Ranpirnase, Rasburicase, Razoxane, Rituximab, Rifampicin, Ritrosulfan, Romurtide, Ruboxistaurin, Sargramostim, Satraplatin, Sirolimus, Sobuzoxane, Sorafenib, Spiromustine, Streptozocin, Sunitinib, Tamoxifen, Tasonermin, Tegafur, Temoporfin, Temozolomide, Teniposide, Testolactone, Thiotepa, Thymalfasin, Tiamiprine, Topotecan, Toremifene, Trail, Trastuzumab, Treosulfan, Triaziquone, Trimetrexate, Triptorelin, Trofosfamide, Uredepa, Valrubicin, Vatalanib, Vandetanib, Verteporfin, Vinblastine, Vincristine, Vindesine, Vinorelbine, Vorozole, Zevalin, or any combination thereof. In some aspects, the anti-cancer agent is a taxane, camptothecin, doxorubicin, michellamine B, vincristine, or platinum compounds such as cisplatin.

In further aspects, a therapeutic agent may be but are not limited to kinase inhibitors such as e.g. Imatinib (Glivec™), ZD-1839/Gefitinib Wessel, Bay43-9006 (Sorafenib, Nexavar™), SU11248/Sunitinib (Sutent™) or OSI-774/Erlotinib (Tarceva™) Dasatinib (SprycellM), Lapatinib (Tykerb™), or, Vatalanib, Vandetanib (Zactima™) or Pazopanib; proteasome inhibitors such as PS-341/Bortezumib (Velcade™); heat shock protein 90 inhibitors like 17-allylaminogeldanamycin (17-AAG); vascular targeting agents (VTAs) like combretastin A4 phosphate or AVE8062/AC7700 and anti-angiogenic drugs like the VEGF antibodies, such as Bevacizumab (Avastin™), or KDR tyrosine kinase inhibitors such as PTK787/ZK222584 (Vatalanib) or Vandetanib (Zactima™) or Pazopanib; monoclonal antibodies such as Trastuzumab (Herceptin™) or Rituximab (MabThera/Rituxan™) or Alemtuzumab (Campath™) or Tositumomab (Bexxar™) or C225/Cetuximab (Erbitux™) or Avastin (see above) or Panitumumab as well as mutants and conjugates of monoclonal antibodies, e.g. Gemtuzumab ozogamicin (Mylotarg™) or Ibritumomab tiuxetan (Zevalin™), and antibody fragments; oligonucleotide based therapeutics like G-3139/Oblimersen (Genasense™); Toll-like receptor/TLR 9 agonists like Promune™, TLR 7 agonists like Imiquimod (Aldara™) or Isatoribine and analogues thereof, or TLR 7/8 agonists like Resiquimod as well as immunostimulatory RNA as TLR 7/8 agonists; protease inhibitors (ix) hormonal therapeutics such as anti-estrogens (e.g. Tamoxifen or Raloxifen), anti-androgens (e.g. Flutamide or Casodex), LHRH analogs (e.g. Leuprolide, Goserelin or Triptorelin) and aromatase inhibitors.

In some aspects, an anti-inflammatory agent is an agent that elicit a biological or medical response in a subject that reduce inflammation (either acute or chronic) or downregulate the immune response, for example, by reducing or inhibiting enzyme or protein activity related to inflammation or an immune response (e.g., inhibition of pro-inflammatory markers or reduction in the production of plasma haptoglobin); by ameliorating one or more symptoms of inflammation or an immune response (e.g., pain, redness, heat or edema); or by slowing or delaying of the inflammatory process or the immune response. In some aspects, an anti-inflammatory agent is anti-inflammatory drug, non-limiting examples of which include glucocorticosteroids, metaproterenol, sulfate, terbutaline, albuterol, bitolterol, pirbuterol, procaterol, salmeterol, BDP, dexamethasone, prednisolone, hydrocortisone, fluoromethazone, medrysone, fluticasone, triamcinolone, flunisolide indomethacin, sulindac, etodolac, mefenamic acid, meclofenamic acid, meclofenamate sodium, flufenamic acid, tolmetin, ketorolac, diclofenac, diclofenac sodium, ibuprofen, naproxen, naproxen sodium, fenoprofen, ketoprofen, flurbiprofen, oxaprozin piroxicam, meloxicam, ampiroxicam, droxicam, pivoxicam, lornoxicam, cinnoxicam, sudoxicam, and tenoxicam.

In some aspects, the polypeptide or protein may be any amino acid, peptide or polypeptide agent from natural, synthetic or recombinant source, including, but not limited to, peptides, polypeptides, and fusion proteins, and wherein such agents may have the biological activity of an enzyme, a structural protein, a DNA-binding protein, a receptor protein, a hormone, a growth factor, a cell cycle dependent protein, or proteins derived or generated to act as inhibitors, as in the case of antibodies, or fragments and artificially constructed antigen binding proteins, or combinations thereof. Those skilled in the art will recognize that numerous methods exist for the preparation, synthesis, isolation, or purification of such agents for use.

Non-limiting examples of anti-metabolite agent that can be used in the delivery system disclosed herein include cytarabine, 5-Azacytidine, gemcitabine (2',2'-Difluorodeoxycytidine), 5-fluorouracil (5-FU), capecitabine, floxuridine, cytarabine, decitabine, and vidaza.

In some aspects, diagnostic agent disclosed herein is a fluorescent agent or a imaging agent. In some aspects, the fluorescent agent, can be selected from, but not limited to fluorescein isothiosyanete (FITC), rhodamine, FAM, luminescent substances such as luminol, luciferin, lucigenin, or fluorescent drug compound (e.g., anthracycline class drugs such as daunorubicin) or any combination thereof. In some aspects, imaging agent is a reporter molecule. For example, a reporter molecule herein can be selected from, but not limited to substituents that allow detection, either directly or indirectly, of compounds at low concentrations. Suitable reporter moieties include, but are not limited to, enzymes, which produce a signal detectable, for example, by colorimetry, fluorescence or luminescence, such as horseradish peroxidase, alkaline phosphatase, beta-galactosidase or glucose-6-phosphate dehydrogenase; chromophores, such as fluorescent, luminescent or dye compounds; groups with an electron density which can be detected by electron microscopy or through their electrical property, such as by conductivity, amperometry, voltammetry, or impedance measurements; and groups which can be detected using optical methods, such as diffraction, surface plasma resonance or contact angle variation, or physical methods, such as atomic force spectroscopy, or the tunnel effect. Other suitable reporter moieties include, but are not limited to, biotin, digoxigenin, peptides, proteins, antibodies, glycoproteins, and sugars. In some aspects, the disclosed delivery system comprises a diagnostic agent. Non-limiting examples of specific binding moieties as diagnostic agents herein include antigen binding domains, growth factors, ligands, or oligonucleotides. In some aspects, the imaging agent may be a radioactive substance. Non-limiting examples of a radioactive substance herein, comprise $^{3}H$, $^{14}C$, $^{32}P$, $^{33}P$, $^{35}S$, $^{123}I$, $^{125}I$, and/or $^{131}I$.

In some aspects, the therapeutic agent, is an agent which modulates the function of pDCs. In such as aspects, the therapeutic agent can be an agent which enhances or decreases IFN production. In certain aspects, the therapeutic agent can be an agent which enhances or decreases IFN alpha production. In some aspects, the therapeutic agent disclosed herein may be an agent which modulate immune response. In some aspects, the therapeutic agent disclosed herein may be an agent which modulate the activity of a T cell. In some aspects, the therapeutic agent can be an agent which can treat or prevent disease, disorder, or pathogenesis associated with abnormal pDCs activity, and/or amount. Non-limiting examples of pDCs associated disease or disorder include systemic lupus erythematosus, autoimmune diseases, cancer, or inflammatory diseases. In certain aspects, pDCs associated disease or disorder include melanoma, ovarian cancer, systemic lupus erythematosus, rheumatoid arthritis, lung cancer, atherosclerosis, multiple myeloma, leukemia, chronic lymphocytic leukemia, chronic myelomonocytic leukemia, breast cancer, hepatocellular carcinoma, gastrointestinal cancer, non-small cell lung carcinoma, psoriasis, or viral infections.

In certain aspects, the delivery system discloses herein may be used for treating, preventing, or reducing the occurrence of autoimmune disease including, without limitation, rheumatoid arthritis (RA), systemic lupus erythematosus (SLE), type I diabetes mellitus, type II diabetes mellitus, multiple sclerosis (MS), immune-mediated infertility such as premature ovarian failure, scleroderma, Sjogren's disease, vitiligo, alopecia (baldness), polyglandular failure, Grave's disease, hypothyroidism, polymyositis, pemphigus vulgaris, pemphigus *foliaceus*, inflammatory bowel disease including Crohn's disease and ulcerative colitis, autoimmune hepatitis including that associated with hepatitis B virus (HBV) and hepatitis C virus (HCV), hypopituitarism, graft-versus-host disease (GvHD), myocarditis, Addison's disease, autoimmune skin diseases, uveitis, pernicious anemia, and hypoparathyroidism, Hashimoto's thyroiditis, Type I and Type II autoimmune polyglandular syndromes, paraneoplastic pemphigus, bullus pemphigoid, dermatitis herpetiformis, linear IgA disease, epidermolysis bullosa acquisita, erythema nodosa, pemphigoid gestationis, cicatricial pemphigoid, mixed essential cryoglobulinemia, chronic bullous disease of childhood, hemolytic anemia, thrombocytopenic purpura, Goodpasture's syndrome, autoimmune neutropenia, myasthenia gravis, Eaton-Lambert myasthenic syndrome, stiff-man syndrome, acute disseminated encephalomyelitis, Guillain-Barre syndrome, chronic inflammatory demyelinating polyradiculoneuropathy, multifocal motor neuropathy with conduction block, chronic neuropathy with monoclonal gammopathy, opsonoclonus-myoclonus syndrome, cerebellar degeneration, encephalomyelitis, retinopathy, primary biliary sclerosis, sclerosing cholangitis, gluten-sensitive enteropathy, ankylosing spondylitis, reactive arthritides, polymyositis/dermatomyositis, mixed connective tissue disease, Bechet's syndrome, psoriasis, polyarteritis nodosa, allergic anguitis and granulomatosis (Churg-Strauss disease), polyangiitis overlap syndrome, hypersensitivity vasculitis, Wegener's granulomatosis, temporal arteritis, Takayasu's arteritis, Kawasaki's disease, isolated vasculitis of the central nervous system, thromboangiutis obliterans, sarcoidosis, glomerulonephritis, or cryopathies.

In some aspects, the therapeutic agent disclosed herein is encapsulated in the delivery system disclosed herein. In some aspects, the therapeutic agent is within the membrane of the delivery system or is attached to the exterior surface of the membrane. The desired amount of the therapeutic agent that is loaded, i.e., encapsulated, in the delivery system herein varies depending on the type of the drug.

C. Compositions

Disclosed herein is a composition comprising the delivery system disclosed herein. In some aspects, the compositions may be used for inducing an immune response in a subject. In one aspect, the compositions include gambogic acid as a targeting moiety to pDCs.

In some aspects, the compositions comprises liposomes, wherein the liposomes comprise a targeting moiety. In some aspects, the compositions comprises liposomes, wherein the liposomes comprise a targeting moiety for delivery of the liposomes to pDCs. In some aspects, the composition comprises liposomes, wherein the liposomes are functionalized with a targeting moiety, and wherein the targeting moiety binds to CD71. In some aspects, the targeting moiety is GA.

In some aspects, the compositions comprises nanoparticles, wherein the nanoparticles comprise a targeting moiety. In some aspects, the compositions comprises nanoparticles, wherein the nanoparticles comprise a targeting moiety for delivery of the nanoparticles to pDCs. In some aspects, the composition comprises nanoparticles, wherein the nanoparticles are functionalized with a targeting moiety, and wherein the targeting moiety binds to CD71. In some aspects, the targeting moiety is GA.

In some aspects, the composition disclosed herein, enhances the delivery of the liposomes or nanoparticles to pDCs cells. In some aspects, the disclosed composition has enhanced the delivery of the liposomes or nanoparticles to pDCs cells by at least by 10% compared to liposomes or nanoparticles without the targeting moiety. In some aspects, the disclosed composition has enhanced delivery of liposomes or nanoparticles by at least about 10%, about 15%, about 20%, about 25%, about 30%, about 35%, about 40%, about 45%, about 50%, about 55%, about 60%, about 65%, about 70%, about 75%, about 80%, about 85%, about 90% or above, to pDCs, compared to compositions comprising liposomes or nanoparticles without the targeting moiety. In some aspects, the composition enhances the delivery of the liposomes or nanoparticles to pDCs cells by at least by about 25% compared to liposomes or nanoparticles without the targeting moiety.

In some aspects, the composition has enhanced delivery of the liposomes or nanoparticles to cells expressing CD71. In some aspects, the composition has enhanced delivery of the liposomes or nanoparticles to cells expressing CD71 by at least by 10% compared to liposomes or nanoparticles without the targeting moiety. In some aspects, the composition has enhanced delivery by at least about 10%, about 15%, about 20%, about 25%, about 30%, about 35%, about 40%, about 45%, about 50%, about 55%, about 60%, about 65%, about 70%, about 75%, about 80%, about 85%, about 90% or above, to cells expressing CD71 compared to composition comprising liposomes or nanoparticles without the targeting moiety. In some aspects, the composition has enhanced delivery of the liposomes or nanoparticles to cells expressing CD71 by at least by about 25% compared to liposomes or nanoparticles without the targeting moiety.

In some aspects, targeting moiety binds to CD71 non-competitively with a natural ligand of CD71. In some aspects, the targeting moiety is GA, and the natural ligand of CD71 is transferrin. In some aspects, the percentage difference in the delivery of liposomes or nanoparticles to pDCs, in the presence of transferrin is less than about 50% compared to the delivery of liposomes or nanoparticles in the absence of transferrin. In some aspects, the percentage difference in the delivery of liposomes or nanoparticles to the pDCs, in the presence of transferrin is less than about 10%, about 15%, about 20%, about 25%, about 30%, about 35%, about 40%, about 45%, about 50%, compared to the delivery of liposomes or nanoparticles in the absence of transferrin.

Pharmaceutical Compositions

In some aspects, the composition disclosed herein can be formulated as a pharmaceutical composition. In some aspects, the pharmaceutical composition comprises a delivery system disclosed herein, preferably for use as a medicament. In some aspects, pharmaceutical compositions comprise liposomes or nanoparticles disclosed herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. The delivery system may be formulated as a single dosage unit or as multiple dosage units.

The compositions comprising delivery system disclosed herein, may be formulated for administration, in any convenient manner, including by compositions for injection, transfusion, or implantation. The compositions described herein may be formulated for subcutaneous, intradermal, intratumoral, intranodal, intramedullar, intramuscular, intravenous (i.v.), or intraperitoneal, injection or adminstration. In some aspects, the disclosed compositions are formulated to be administered by intradermal or subcutaneous injection. In some aspects, the disclosed compositions are formulated to be administered by i.v. injection. The compositions may also be formulated, to be injected directly into a tumor, lymph node, or site of infection. In some aspects, the compositions disclosed herein are formulated for intravenous administration.

In some aspects, the compositions, compositions disclosed herein may further compromise one or more pharmaceutically acceptable diluent(s), excipient(s), and/or carrier(s). Pharmaceutically acceptable diluents, carriers, and excipients can include, but are not limited to, physiological saline, Ringer's solution, phosphate solution or buffer, buffered saline, and other carriers known in the art. Pharmaceutically acceptable carriers include any and all solvents, adjuvants, dispersion media, coatings, surfactants, antioxidants, preservatives (e.g., antibacterial agents, antifungal agents), isotonic agents, absorption delaying agents, salts, drugs, drug stabilizers, gels, binders, excipients, disintegration agents, lubricants, sweetening agents, flavoring agents, dyes, colorants, other medicinal or pharmaceutical agents, wetting agents, emulsifying agents, solution promoters, solubilizers, antifoaming agents, and such like materials and any combinations thereof, as would be known to one of ordinary skill in the art. (See, e.g., Remington's Pharma. Sci. 18th ed. 1990). Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols. Techniques for formulation and administration of drugs may also be found for example in Remington's Pharma. Sci. 18th ed. 1990. Except insofar as any conventional carrier is incompatible with the active ingredient, its use in the therapeutic or pharmaceutical compositions is contemplated. In certain embodiments, a pharmaceutical composition described herein comprising a delivery system herein, further comprises a suitable amount of an antifungal agent. In some cases, a pharmaceutical composition described herein comprises an antifungal agent in an amount sufficient for the pharmaceutical composition to retain at least 20%, 30%, 40%, 50%, 60%, 70%, 80% or 90% of its desired activity for a period of at least 1 month, 2 months, 3 months, 6 months, 1 year, 1.5 years, 2 years, 2.5 years or 3 years.

In certain aspects, pharmaceutical compositions described herein may be formulated in conventional manner using one or more physiologically acceptable carriers comprising excipients and auxiliaries to facilitate processing of engineered cells or vectors into preparations which can be used pharmaceutically. In some aspects, any of the well-known techniques, carriers, and excipients may be used as suitable and/or as understood in the art.

In certain aspects, pharmaceutical compositions described herein may be an aqueous suspension comprising one or more polymers as suspending agents. In some aspects, polymers that may comprise pharmaceutical compositions described herein include: water-soluble polymers such as cellulosic polymers, e.g., hydroxypropyl methylcellulose; water-insoluble polymers such as cross-linked carboxyl-containing polymers; mucoadhesive polymers, selected from, for example, carboxymethylcellulose, carbomer (acrylic acid polymer), poly(methylmethacrylate), polyacrylamide, polycarbophil, acrylic acid/butyl acrylate copolymer, sodium alginate, and dextran; or a combination thereof. In some aspects, pharmaceutical compositions disclosed herein may comprise at least 5%, at least 10%, at least 20%, at least 25%, at least 30%, at least 35%, at least 40%, at least 45%, or at least 50% total amount of polymers as suspending agent(s) by total weight of the composition. In some aspects, pharmaceutical compositions disclosed herein may comprise about 5% to about 99%, about 10%, about 95%, or about 15% to about 90% total amount of polymers as suspending agent(s) by total weight of the composition.

In certain aspects, pharmaceutical compositions disclosed herein may comprise a viscous formulation. In some aspects, viscosity of composition herein may be increased by the addition of one or more gelling or thickening agents. In some aspects, compositions disclosed herein may comprise one or more gelling or thickening agents in an amount to provide a sufficiently viscous formulation to remain on treated tissue. In some aspects, pharmaceutical compositions disclosed herein may comprise at least 5%, at least 10%, at least 20%, at least 25%, at least 30%, at least 35%, at least 40%, at least 45%, or at least 50% total amount of gelling or thickening agent(s) by total weight of the composition. In some aspects, pharmaceutical compositions disclosed herein may comprise about 5% to about 99%, about 10%, about 95%, or about 15% to about 90% total amount of gelling or thickening agent(s) by total weight of the composition. In some aspects, suitable thickening agents for use herein can be hydroxypropyl methylcellulose, hydroxyethyl cellulose, polyvinylpyrrolidone, carboxymethyl cellulose, polyvinyl alcohol, sodium chondroitin sulfate, sodium hyaluronate. In other aspects, viscosity enhancing agents can be acacia (gum arabic), agar, aluminum magnesium silicate, sodium alginate, sodium stearate, bladderwrack, bentonite, carbomer, carrageenan, Carbopol, xanthan, cellulose, microcrystalline cellulose (MCC), *ceratonia*, chitin, carboxymethylated chitosan, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly (methoxyethyl methacrylate), poly(methoxyethoxyethyl methacrylate), hydroxypropyl cellulose, hydroxypropylmethyl-cellulose (HPMC), sodium carboxymethyl-cellulose (CMC), silicon dioxide, polyvinylpyrrolidone (PVP: povidone), Splenda® (dextrose, maltodextrin and sucralose), or any combination thereof.

In certain aspects, pharmaceutical compositions disclosed herein may comprise additional agents or additives selected from a group including surface-active agents, detergents, solvents, acidifying agents, alkalizing agents, buffering agents, tonicity modifying agents, ionic additives effective to increase the ionic strength of the solution, antimicrobial agents, antibiotic agents, antifungal agents, antioxidants, preservatives, electrolytes, antifoaming agents, oils, stabilizers, enhancing agents, and the like. In some aspects, pharmaceutical compositions disclosed herein may comprise at least 5%, at least 10%, at least 20%, at least 25%, at least 30%, at least 35%, at least 40%, at least 45%, or at least 50% total amount of one or more agents by total weight of the composition. In some aspects, pharmaceutical compositions disclosed herein may comprise about 5% to about 99%, about 10%, about 95%, or about 15% to about 90% total amount of one or more agents by total weight of the composition. In some aspects, one or more of these agents may be added to improve the performance, efficacy, safety, shelf-life and/or other property of the muscarinic antagonist composition of the present disclosure. In some aspects, additives may be biocompatible, without being harsh, abrasive, and/or allergenic.

In certain aspects, pharmaceutical compositions disclosed herein may comprise one or more acidifying agents. As used herein, "acidifying agents" refers to compounds used to provide an acidic medium. Such compounds include, by way of example and without limitation, acetic acid, amino acid, citric acid, fumaric acid and other alpha hydroxy acids, such as hydrochloric acid, ascorbic acid, and nitric acid and others known to those of ordinary skill in the art. In some aspects, any pharmaceutically acceptable organic or inorganic acid may be used. In some aspects, pharmaceutical compositions disclosed herein may comprise at least 5%, at least 10%, at least 20%, at least 25%, at least 30%, at least 35%, at least 40%, at least 45%, at least 50% total amount of one or more acidifying agents by total weight of the composition. In some aspects, pharmaceutical compositions disclosed herein may comprise about 5% to about 99%, about 10%, about 95%, or about 15% to about 90% total amount of one or more acidifying agents by total weight of the composition.

In certain aspects, pharmaceutical compositions disclosed herein may comprise one or more alkalizing agents. As used herein, "alkalizing agents" are compounds used to provide alkaline medium. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, and trolamine and others known to those of ordinary skill in the art. In some aspects, any pharmaceutically acceptable organic or inorganic base can be used. In some aspects, pharmaceutical compositions disclosed herein may comprise at least 5%, at least 10%, at least 20%, at least 25%, at least 30%, at least 35%, at least 40%, at least 45%, at least 50% total amount of one or more alkalizing agents by total weight of the composition. In some aspects, pharmaceutical compositions disclosed herein may comprise about 5% to about 99%, about 10%, about 95%, or about 15% to about 90% total amount of one or more alkalizing agents by total weight of the composition.

In certain aspects, pharmaceutical compositions disclosed herein may comprise one or more antioxidants. As used herein, "antioxidants" are agents that inhibit oxidation and thus can be used to prevent the deterioration of preparations by the oxidative process. Such compounds include, by way of example and without limitation, ascorbic acid, ascorbyl palmitate, butylated hydroxyanisole, butylated hydroxytoluene, hypophophorous acid, monothioglycerol, propyl gallate, sodium ascorbate, sodium bisulfite, sodium formaldehyde sulfoxylate, sodium metabisulfite and other materials known to one of ordinary skill in the art. In some aspects, pharmaceutical compositions disclosed herein may comprise at least 5%, at least 10%, at least 20%, at least 25%, at least 30%, at least 35%, at least 40%, at least 45%, at least 50% total amount of one or more antioxidants by total weight of the composition. In some aspects, pharmaceutical compositions disclosed herein may comprise about 5% to about 99%, about 10%, about 95%, or about 15% to about 90% total amount of one or more antioxidants by total weight of the composition.

In certain aspects, pharmaceutical compositions disclosed herein may comprise a buffer system. As used herein, a "buffer system" is a composition comprised of one or more buffering agents wherein "buffering agents" are compounds used to resist change in pH upon dilution or addition of acid or alkali. Buffering agents include, by way of example and without limitation, potassium metaphosphate, potassium phosphate, monobasic sodium acetate and sodium citrate anhydrous and dihydrate and other materials known to one of ordinary skill in the art. In some aspects, any pharmaceutically acceptable organic or inorganic buffer can be used. In some aspects, pharmaceutical compositions disclosed herein may comprise at least 5%, at least 10%, at least 20%, at least 25%, at least 30%, at least 35%, at least 40%, at least 45%, at least 50% total amount of one or more buffering agents by total weight of the composition. In some aspects, pharmaceutical compositions disclosed herein may comprise about 5% to about 99%, about 10%, about 95%, or about 15% to about 90% total amount of one or more buffering agents by total weight of the composition.

In some aspects, the amount of one or more buffering agents may depend on the desired pH level of a composition. In some aspects, pharmaceutical compositions disclosed herein may have a pH of about 6 to about 9. In some aspects, pharmaceutical compositions disclosed herein may have a pH greater than about 8, greater than about 7.5, greater than about 7, greater than about 6.5, or greater than about 6.

In certain aspects, pharmaceutical compositions disclosed herein may comprise one or more preservatives. As used herein, "preservatives" refers to agents or combination of agents that inhibits, reduces or eliminates bacterial growth in a pharmaceutical dosage form. Non-limiting examples of preservatives include Nipagin, Nipasol, isopropyl alcohol and a combination thereof. In some aspects, any pharmaceutically acceptable preservative can be used. In some aspects, pharmaceutical compositions disclosed herein may comprise at least 5%, at least 10%, at least 20%, at least 25%, at least 30%, at least 35%, at least 40%, at least 45%, at least 50% total amount of one or more preservatives by total weight of the composition. In some aspects, pharmaceutical compositions disclosed herein may comprise about 5% to about 99%, about 10%, about 95%, or about 15% to about 90% total amount of one or more preservatives by total weight of the composition.

In certain aspects, pharmaceutical compositions disclosed herein may comprise one or more surface-acting reagents or detergents. In some aspects, surface-acting reagents or detergents may be synthetic, natural, or semi-synthetic. In some aspects, compositions disclosed herein may comprise anionic detergents, cationic detergents, zwitterionic detergents, ampholytic detergents, amphoteric detergents, non-ionic detergents having a steroid skeleton, or a combination thereof. In some aspects, pharmaceutical compositions disclosed herein may comprise at least 5%, at least 10%, at least 20%, at least 25%, at least 30%, at least 35%, at least 40%, at least 45%, at least 50% total amount of one or more surface-acting reagents or detergents by total weight of the composition. In some aspects, pharmaceutical compositions disclosed herein may comprise about 5% to about 99%, about 10%, about 95%, or about 15% to about 90% total amount of one or more surface-acting reagents or detergents by total weight of the composition.

In certain aspects, pharmaceutical compositions disclosed herein may comprise one or more stabilizers. As used herein, a "stabilizer" refers to a compound used to stabilize an active agent against physical, chemical, or biochemical process that would otherwise reduce the therapeutic activity of the agent. Suitable stabilizers include, by way of example and without limitation, succinic anhydride, albumin, sialic acid, creatinine, glycine and other amino acids, niacinamide, sodium acetyltryptophonate, zinc oxide, sucrose, glucose, lactose, sorbitol, mannitol, glycerol, polyethylene glycols, sodium caprylate and sodium saccharin and others known to those of ordinary skill in the art. In some aspects, pharmaceutical compositions disclosed herein may comprise at least 5%, at least 10%, at least 20%, at least 25%, at least 30%, at least 35%, at least 40%, at least 45%, at least 50% total amount of one or more stabilizers by total weight of the composition. In some aspects, pharmaceutical compositions disclosed herein may comprise about 5% to about 99%, about 10%, about 95%, or about 15% to about 90% total amount of one or more stabilizers by total weight of the composition.

In some aspects, pharmaceutical compositions disclosed herein may comprise one or more tonicity agents. As used herein, a "tonicity agents" refers to a compound that can be used to adjust the tonicity of the liquid formulation. Suitable tonicity agents include, but are not limited to, glycerin, lactose, mannitol, dextrose, sodium chloride, sodium sulfate, sorbitol, trehalose and others known to those or ordinary skill in the art. Osmolarity in a composition may be expressed in milliosmoles per liter (mOsm/L).

Osmolarity may be measured using methods commonly known in the art. In some aspects, a vapor pressure depression method is used to calculate the osmolarity of the compositions disclosed herein. In some aspects, the amount of one or more tonicity agents comprising a pharmaceutical composition disclosed herein may result in a composition osmolarity of about 150 mOsm/L to about 500 mOsm/L, about 250 mOsm/L to about 500 mOsm/L, about 250 mOsm/L to about 350 mOsm/L, about 280 mOsm/L to about 370 mOsm/L or about 250 mOsm/L to about 320 mOsm/L. In some aspects, a composition herein may have an osmolality ranging from about 100 mOsm/kg to about 1000 mOsm/kg, from about 200 mOsm/kg to about 800 mOsm/kg, from about 250 mOsm/kg to about 500 mOsm/kg, or from about 250 mOsm/kg to about 320 mOsm/kg, or from about 250 mOsm/kg to about 350 mOsm/kg or from about 280 mOsm/kg to about 320 mOsm/kg. In some aspects, a pharmaceutical composition described herein may have an osmolarity of about 100 mOsm/L to about 1000 mOsm/L, about 200 mOsm/L to about 800 mOsm/L, about 250 mOsm/L to about 500 mOsm/L, about 250 mOsm/L to about 350 mOsm/L, about 250 mOsm/L to about 320 mOsm/L, or about 280 mOsm/L to about 320 mOsm/L. In some aspects, pharmaceutical compositions disclosed herein may comprise at least 5%, at least 10%, at least 20%, at least 25%, at least 30%, at least 35%, at least 40%, at least 45%, at least 50% total amount of one or more tonicity modifiers by total weight of the composition. In some aspects, pharmaceutical compositions disclosed herein may comprise about 5% to about 99%, about 10%, about 95%, or about 15% to about 90% total amount of one or more tonicity modifiers by total weight of the composition.

In some aspect, the pharmaceutical composition may comprise one or more active agents in addition to the therapeutic agents loaded in the delivery system provided herein. Non limiting examples of additional active agents include but are not restricted to antibiotics, anti-pyrectics, antimicrobials, antifungals, NSAIDs, chemotherapeutic and anticancer agents.

The actual dosage amount of a composition according to the present disclosure, and the selection of any combination treatment to be administered to a subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

D. Methods of Use

Further disclosed herein are methods of using the disclosed delivery system. In some aspects, the liposomes comprise a cargo comprising the therapeutic agent within or bound to the liposomes or nanoparticles and are targeted to pDCs via the targeting moiety GA. The therapeutic agent can be a nucleic acid, an antiviral agent, an antibacterial agent, an antifungal agent, an antimetabolic agent, an anti-cancer agent, anti-inflammatory agent, a polypeptide, a protein, or a diagnostic agent.

Method of Targeted Delivery

In some aspects, disclosed herein is a method of targeted delivery of liposomes or nanoparticles herein. In some aspects, the method comprises targeted delivery of the disclosed liposomes or nanoparticles to cells expressing CD71. In some aspects, the cells that express CD71 comprise pDCs. In some aspects, the method comprises targeted delivery of the disclosed liposomes or nanoparticles to pDCs cells. In some aspects, the liposomes or nanoparticles for the targeted delivery comprises a targeting moiety that binds to CD71. In some aspects, the targeting moiety is GA. In some aspects, the liposomes or nanoparticles are functionalized with GA and the method of targeted delivery comprises administering a composition comprising the GA functionalized liposomes or nanoparticles in a subject in need thereof.

In some aspects, the method of targeted delivery results in enhanced uptake of GA functionalized liposomes or nanoparticles by pDCs in a subject by at least 10% more compared to liposomes or nanoparticles without the targeting moiety. In some aspects, the uptake of liposomes or nanoparticles is enhanced in pDCs by at least about 10%, about 15%, about 20%, about 25%, about 30%, about 35%, about 40%, about 45%, about 50%, about 55%, about 60%, about 65%, about 70%, about 75%, about 80%, about 85%, about 90% or above, compared to liposomes or nanoparticles without the targeting moiety. In some aspects, the targeting moiety enhances the uptake of the liposomes or nanoparticles to pDCs by at least by about 25% compared to liposomes or nanoparticles without the targeting moiety.

In some aspects, the method of targeted delivery results in enhanced uptake of GA functionalized liposomes or nanoparticles by cells expressing CD71 in a subject by at least 10% more compared to liposomes or nanoparticles without the targeting moiety. In some aspects, the uptake of liposomes or nanoparticles is enhanced in cells expressing CD71 by at least about 10%, about 15%, about 20%, about 25%, about 30%, about 35%, about 40%, about 45%, about 50%, about 55%, about 60%, about 65%, about 70%, about 75%, about 80%, about 85%, about 90% or above, compared to liposomes or nanoparticles without the targeting moiety. In some aspects, the targeting moiety enhances the uptake of the liposomes or nanoparticles to cells expressing CD71 by at least by about 25% compared to liposomes or nanoparticles without the targeting moiety.

In some aspects, the method of targeted delivery results in uptake of the liposomes or nanoparticles in a non-competitive manner with a natural ligand of CD71. In some aspects, the targeting moiety is GA, and the natural ligand of CD71 is transferrin. In some aspects, the percentage difference in the uptake of liposomes or nanoparticles in pDCs, in the presence of transferrin is less than about 50% compared to the uptake of liposomes or nanoparticles in the absence of transferrin. In some aspects, the percentage difference in the uptake of liposomes or nanoparticles to the pDCs, in the presence of transferrin is less than about 10%, about 15%, about 20%, about 25%, about 30%, about 35%, about 40%, about 45%, about 50%, compared to the uptake of liposomes or nanoparticles in the absence of transferrin.

Method of Treatment

In some aspects, provided herein is a method of treatment using the delivery system disclosed herein, to treat, prevent, or reduce occurrence of a disease or disorder in a subject. In some aspects, the method comprises administering to the subject an effective amount of a composition comprising liposomes or nanoparticles disclosed herein. In some aspects, the liposomes or nanoparticles comprises a targeting moiety that binds to CD71. In some aspects, the targeting moiety is GA. In some aspects, the liposomes or nanoparticles are functionalized with GA and the method of treatment comprises administering an effective amount of composition comprising the GA functionalized liposomes or nanoparticles in a subject in need thereof.

In some aspects, the delivery system disclosed herein, is used in a method to treat, prevent, or reduce occurrence of a cancer, autoimmune disease, inflammatory disease, viral infection, bacterial infection, or a fungal infection.

In some aspects, the cancer that can be treated using the disclosed method can be acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sezary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-Cell lymphoma (cutaneous), testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), unknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood). In some aspects, the cancer is a melanoma, ovarian cancer, lung cancer, multiple myeloma, leukemia, chronic lymphocytic leukemia, chronic myelomonocytic leukemia, breast cancer, hepatocellular carcinoma, gastrointestinal cancer, or non-small cell lung carcinoma.

In some aspects, the disclosed method can be used to treat, prevent, or reduce occurrence of an inflammatory disease including, but are not limited to, arthritis, inflammatory bowel disease, asthma, psoriasis, organ transplant rejections, radiation-induced injury, cancer, lupus and other autoimmune disorders, burns, trauma, stroke, rheumatic disorders, renal diseases, allergic diseases, infectious diseases, ocular diseases, skin diseases, gastrointestinal diseases, hepatic diseases, cerebral edema, sarcoidosis, thrombocytopenia, spinal cord injury, and autoimmune disorders.

In some aspects, the disclosed method can be used to treat, prevent, or reduce occurrence of autoimmune disease including, without limitation, rheumatoid arthritis (RA), systemic lupus erythematosus (SLE), type I diabetes mellitus, type II diabetes mellitus, multiple sclerosis (MS), immune-mediated infertility such as premature ovarian failure, scleroderma, Sjogren's disease, vitiligo, alopecia (baldness), polyglandular failure, Grave's disease, hypothyroidism, polymyositis, pemphigus vulgaris, pemphigus *foliaceus*, inflammatory bowel disease including Crohn's disease and ulcerative colitis, autoimmune hepatitis including that associated with hepatitis B virus (HBV) and hepatitis C virus (HCV), hypopituitarism, graft-versus-host disease (GvHD), myocarditis, Addison's disease, autoimmune skin diseases, uveitis, pernicious anemia, and hypoparathyroidism, Hashimoto's thyroiditis, Type I and Type II autoimmune polyglandular syndromes, paraneoplastic pemphigus, bullus pemphigoid, dermatitis herpetiformis, linear IgA disease, epidermolysis bullosa acquisita, erythema nodosa, pemphigoid gestationis, cicatricial pemphigoid, mixed essential cryoglobulinemia, chronic bullous disease of childhood, hemolytic anemia, thrombocytopenic purpura, Goodpasture's syndrome, autoimmune neutropenia, myasthenia gravis, Eaton-Lambert myasthenic syndrome, stiff-man syndrome, acute disseminated encephalomyelitis, Guillain-Barre syndrome, chronic inflammatory demyelinating polyradiculoneuropathy, multifocal motor neuropathy with conduction block, chronic neuropathy with monoclonal gammopathy, opsonoclonus-myoclonus syndrome, cerebellar degeneration, encephalomyelitis, retinopathy, primary biliary sclerosis, sclerosing cholangitis, gluten-sensitive enteropathy, ankylosing spondylitis, reactive arthritides, polymyositis/dermatomyositis, mixed connective tissue disease, Bechet's syndrome, psoriasis, polyarteritis nodosa, allergic anguitis and granulomatosis (Churg-Strauss disease), polyangiitis overlap syndrome, hypersensitivity vasculitis, Wegener's granulomatosis, temporal arteritis, Takayasu's arteritis, Kawasaki's disease, isolated vasculitis of the central nervous system, thromboangiutis obliterans, sarcoidosis, glomerulonephritis, or cryopathies.

In some aspects, the disclosed method can be used to treat, prevent, or reduce occurrence of a viral infection including infection caused by herpesviruses such as herpes simplex virus type 1 (HSV-1), herpes simplex virus type 2 (HSV-2), varicella-zoster virus (VZV) and cytomegalovirus (CMV), viruses belonging to the family Orthomyxoviridae such as viruses belonging to the family (collectively referred to as herpes viruses), influenza A viruses, influenza B viruses, influenza C viruses (collectively referred to as influenza viruses), human immunodeficiency Viruses belonging to retroviridae such as virus (HIV), viruses belonging to paramyxoviridae such as measles virus and mumps virus, viruses belonging to picornaviridae such as poliovirus, rhinovirus and hepatitis A virus, type B Viruses belonging to the family Hepadnaviridae such as flame virus, viruses belonging to Flaviviridae such as hepatitis C virus, Japanese encephalitis virus and West Nile virus, viruses belonging to the adenoviridae family such as human adenovirus, coronavirus, SARS virus, viruses belonging to the Coronaviridae family such as COVID19, viruses belonging to the Togaviridae family such as rubella virus, viruses belonging to the Rhabdoviridae family such as rabies virus and vesicular stomatitis virus, viruses belonging to the Filoviridae family such as Ebola virus, and human papillomaviruses, viruses belonging to the family of papovaviridae such as (HPV).

In some aspects, the disclosed method can be used to treat, prevent, or reduce occurrence of a bacterial infection including infection caused by *Moraxella* spp., Costridium spp., *Corynebacterium* spp., Diplococcus spp., *Flavobacterium* spp., Hemophilus spp., *Klebsiella* spp., Leptospira spp., *Mycobacterium* spp., *Neisseria* spp., *Propionibacterium* spp., *Proteus* spp., *Pseudomonas* spp., *Serratia* spp., *Escherichia* spp., *Staphylococcus* spp., *Streptococcus* spp., and bacteria-like organisms including *Mycoplasma* spp. and *Rickettsia* spp. In some aspects, the antibacterial agent may be an antibiotic, non-limiting examples of which include penicillin, ampicillin, netacillin, carbencillin, tetracycline, tetracycline hydrochloride, oxtetracycline hydrochloride, chlortetracycline hydrochloride, 7-chloro-6-dimethyltetracycline, doxycycline, doxycycline monohydrate, methacycline hydrochloride, minocycline hydrochloride, rolitetracycline, dihydrostreptomycin, streptomycin, gentamicin, kanamycin, neomycin, erythromycin, carbomycin, oleandomycin, troleandomycin, Polymysin B, collistin, cephalothin sodium, cephaloridine, cephaloglycin dehydrate, cephalexin monohydrate, or any combination thereof.

In some aspects, the disclosed method can be used to treat, prevent, or reduce occurrence of a fungal infection including infection caused by any pathogenic or opportunistic fungi, including those from the genera *Candida, Aspergillus, Cryptococcus, Histoplasma, Pneumocystis, Coccidioides* Mycetoma, *Paracoccidioides*, and Stachybotrys, each of which is among prominent fungal pathogens. Species such as *C. albicans, Aspergillus fumigatus, Aspergillus clavatus, Cryptococcus neoformans, Cryptococcus laurentii, Cryptococcus albidus, Cryptococcus gattii, Histoplasma capsulatum, Pneumocystis carinii*, or Stachybotrys chartarum. In some aspects, the antifungal agent may be an anti-fungal drug non-limiting example of which include Amphotericin B, Candicidin, Filipin, Hamycin, Natamycin, Nystatin, Rimocidin, Bifonazole, Butoconazole, Clotrimazole, Econazole, Fenticonazole, Isoconazole, Ketoconazole, Miconazole, Omoconazole, Oxiconazole, Sertaconazole, Sulconazole, Tioconazole, Albaconazole, Fluconazole, Isavuconazole, Itraconazole, Posaconazole, Ravuconazole, Terconazole, Voriconazole, Abafungin, Amorolfin, Butenafine, Naftifine, Terbinafine, Anidulafungin, Caspofungin, Micafungin, Ciclopirox, Flucytosine, Griseofulvin, Haloprogin, Polygodial, Tolnaftate, Undecylenic acid, or any combination thereof.

In some aspects, the disclosed method can be used to treat, prevent, or reduce occurrence of pDCs associated disease or disorder. Non-limiting examples of pdCs associated disease or disorder include systemic lupus erythematosus, autoimmune diseases, cancer, or inflammatory diseases. In certain aspects, pDCs associated disease or disorder include melanoma, ovarian cancer, systemic lupus erythematosus, rheumatoid arthritis, lung cancer, atherosclerosis, multiple myeloma, leukemia, chronic lymphocytic leukemia, chronic myelomonocytic leukemia, breast cancer, hepatocellular carcinoma, gastrointestinal cancer, non-small cell lung carcinoma, psoriasis, or viral infections.

In some aspects, the disclosed method can be used to treat, prevent, or reduce occurrence of disease or disorder associated with enhanced or decreased IFN production. In certain aspects, the disease or disorder is associated with enhanced or decreased IFN alpha production. In some aspects, the disclosed method can be used to modulate immune response in a subject. In some aspects, the disclosed method can be used to modulate the activity of a T cell in a subject.

In further aspects, provided herein is a method of vaccinating a subject in need thereof comprising administering an effective amount composition in a subject in need thereof. In such aspects, the method of vaccinating can be used to or reduce occurrence of disease or disorder associated with cancer, autoimmune disease, viral infection, bacterial infection, or fungal infection.

Method of Diagnosis

In certain aspects, provided herein is a method of diagnosis using the disclosed delivery system. In some aspects, the method of diagnosis can comprise delivering liposomes or nanoparticles comprising a diagnostic agent to cells in a subject to allow for the identification of target cells. In some aspects, the method comprises delivery of the disclosed liposomes or nanoparticles wherein the target cells express CD71. In some aspects, the target cells that express CD71 comprise pDCs. In some aspects, the method comprises delivery of the disclosed liposomes or nanoparticles to pDCs cells. In some aspects, the liposomes or nanoparticles comprises a targeting moiety that binds to CD71. In some aspects, the targeting moiety is GA. In some aspects, the liposomes or nanoparticles are functionalized with GA and the method of diagnosis comprises administering a composition comprising GA functionalized liposomes or nanoparticles, in a subject in need thereof. In such aspects, the GA functionalized liposomes or nanoparticles may further comprise a diagnostic agent.

In certain aspects, liposomes or nanoparticles herein may be detectably labeled by linking to a detectable marker moiety such as a fluorescent label, an electron dense substance, a reporter moiety, a specific or nonspecific binding moiety, a radioactive, or other detectable moiety as described in Section B, and that one of skill in the art deems to be appropriate for the particular disease that is to be detected and diagnosed by the method of the disclosure. The quantity of the delivery vehicle of the disclosure that is administered for a diagnostic purpose should include an effective amount of the diagnostic label for the intended purpose. Such amounts can be determined empirically, and are also well known in the art.

In some aspects, the delivery system disclosed herein can be used to quantitatively or qualitatively assess pDCs activity or concentration in vitro or in vivo. In such aspects, the method comprises using a composition comprising GA functionalized liposomes or nanoparticles, in vitro or in vivo. In some aspects, the GA functionalized liposomes or nanoparticles may further comprise a diagnostic agent as described in Section B. In some aspects, the uptake of GA functionalized liposomes or nanoparticles may be assessed. In further aspects, the method can further comprise analyzing pDCs of a subject by determining whether GA functionalized liposomes or nanoparticles is present in pDCs of the subject. In some aspects, the described methods may be performed by analyzing a biological sample obtained from a subject. Methods for carrying out an analysis of this nature are known to those skilled in the art. Some examples of such methods include electron microscopy, fluorescence microscopy or computed axial tomography (i.e., CAT scan).

In some aspects, GA functionalized liposomes or nanoparticles comprising a diagnostic agent together with therapeutic agent, can be used in monitoring of the delivery and distribution of the therapeutic agent. In further aspects, GA functionalized liposomes or nanoparticles described herein can be used for monitoring the therapeutic efficiency of a treatment or disease progression.

E. Kits

The disclosure further encompasses a kit comprising a delivery system described herein. In some aspects, the kit may comprise GA functionalized liposomes or nanoparticles ready for the use. In some aspects, the kit may comprise a composition comprising GA functionalized liposomes or nanoparticles. In some aspects, the kit may comprise a pharmaceutical composition comprising GA functionalized liposomes or nanoparticles. In further aspects, the kit may further comprise GA functionalized liposomes or nanoparticles and one or more therapeutic or diagnostic agent for addition to the liposomes or nanoparticles. In another aspect, the kit may comprise GA functionalized liposomes or nanoparticles, each containing a specific therapeutic or diagnostic agent for the treatment, diagnosis or monitoring of a particular disease or condition. In some aspects, the kits can further comprise instructions for use. For example, a kit comprising an instruction for using the kit can or cannot physically include the instruction with other individual components. Instead, the instruction can be supplied as a separate component, either in a paper form or an electronic form which can be supplied on computer readable memory device or downloaded from an internet website, or as recorded presentation. In some aspects, a kit for use in a disclosed method can comprise one or more containers holding GA functionalized liposomes or nanoparticles or package insert with instructions for use. In an aspect, suitable containers include, for example, bottles, vials, bags, etc. The containers can be formed from a variety of materials such as glass or plastic. The container can hold GA functionalized liposomes or nanoparticles, and can have a sterile access port. In an aspect, a disclosed kit can comprise a "package insert". In an aspect, a package insert can refer to instructions, that contain information about the methods and usage. The label or package insert can describe how a disclosed component can be used. A kit can comprise additional components necessary for GA functionalized liposomes or nanoparticles such as, for example, other buffers, or diluents.

EXAMPLES

The Examples that follow are illustrative of specific aspects of the invention, and various uses thereof. They set forth for explanatory purposes only and are not to be taken as limiting the invention.

Methods

Inbred mice and distribution of dendritic cells: BL/6, SV129 and BALB/6 inbred mouse lines were obtained from Jackson Laboratory (Bar Harbor, ME) The distribution of dendritic cells were examined using flow cytometry by using fluorochrome-conjugated monoclonal antibodies. Briefly, cells from spleen and liver were isolated from the mice and stained using fluorophore labeled antibodies. Cells were then fixed using 4% paraformaldehyde and analyzed by flow cytometry.

CD71 Robust SD measurements: CD71 expression was measured using flow cytometry. After isolation, cells were made into a single cell suspension and stained using fluorochrome-conjugated antibodies. CD71 surface expression in particular was measured using anti-CD71 antibodies. CD71 expression at the population level was quantified using either the mean or median fluorescence intensity of a population of cells. Robust SD was calculated by taking the standard deviation of fluorescence of the middle 67% of cells within a population.

Single cell suspension: RPMI medium was prepared combining 10% heat-inactivated fetal bovine serum (FBS), 2 mM L-glutamine, penicillin (100 IU/ml)/streptomycin (100 μg/ml), 55 μM 2-mercaptoethanol. Spleen and lymph nodes were removed aseptically from euthanized mice, and placed in 15 ml tubes containing 5 ml ice-cold RPMI/FBS (RPMI with 2% FBS) or Balanced Salt Solution/FBS (BSS/FBS). NOTE: Since BSS prevents efficient RBC lysis, use RPMI for the preparation of the splenic cell suspension and switch to BSS after RBC lysis. The organ was placed in between two pieces of sterile 100 μm cell strainer mesh in a petri dish containing 2 ml ice-cold RPMI/FBS or BSS/FBS and mashes until it has been torn into very fine parts. The cell suspension was transferred to a 15 ml tube and spun down at 453×g for 5 min at 4° C. The supernatant was removed. The cells were resuspended with 1 ml RBC lysis buffer for every 108 cells and incubate at RT for 3-4 min. RBC lysis was stopped with 14 ml ice-cold BSS/FBS and cells were spin down at 453×g for 5 min at 4° C. The cells were labeled using phycoerythrin (PE)-conjugated antibodies and analyzed using flow cytometry.

Synthesis of Functionalized liposomes: Liposomes were synthesized using the thin-film rehydration method. GA-modified DSPE (1,2-distearoyl-sn-glycero-3-phosphorylethanolamine) was synthesized using copper catalyzed azide-alkynecyclo addition between GA-alkyne and DSPE-[PEG2000]-azide (FIG. 4A).

Uptake measurements: Uptake of liposomes was measured using flow cytometry. Constructs were labeled with a fluorescent dye and cells were treated with a suspension of fluorescent construct for times ranging up to 18 h. After treatment cells were made into a single cell suspension and analyzed using flow cytometry. The typical uptake of the construct by a cell population was determined using either the mean or median fluorescence intensity of the fluorescence channel corresponding to the fluorophore used to label the construct or the fraction of cells with a fluorescence intensity in that channel that exceeded a defined threshold.

Competition assay: Competition effects were determined similarly to uptake by comparing populations of cells treated identically with the construct in the presence or absence of physiological concentrations of mouse holotransferrin, the natural ligand of CD71. The fractional change in uptake of the construct was calculated and used to determine the degree to which holotransferrin binding competed with uptake of the construct.

Synthesis of functionalized nanoparticles: The GA-functionalized NP's were synthesized by first modifying the alginate material with tetrabutylammonium. This was done by first letting 2 g of alginate react in 60 mL of a 1:1 mixture of ethanol:0.6N HCl overnight at 4C. Then after the alginate was recovered and dried it was dispersed in 100 mL of water and tetrabutylammonium hydroxide was added dropwise until the polymer dissolved completely. After the alginate was purified by dialysis and recovered by lyophilization to create TBA-alginate. GA was reacted with an excels of propargylamine in the presence of a 2× molar excels of dicyclohyxylcarbodiimide in dichloromethane at 4 C overnight. Byproducts were extracted with water and the solution of GA-propargylamine was dries with sodium sulfate. The GA-propargylamine was ligated to 4-azidoaniline using copper catalyzed click chemistry stirring at room temperature in 3:1 tetrahydrofuran:dichloromethane to create GA-amine. The GA-amine and TBA-alginate were co-dissolved in dichloromethane at a 2:1 molar ratio GA-amine:alginate monomer and ligated using a 2× molar excess of dicyclohexylcarbodiimide at 4 C overnight. The product, GA-alginate, was purified by dialysis and recovered by lyophilization. Nanoparticles were formed by adding a 1% solution of GA-alginate in water to a 10% solution of CaCl stirred at 800 RPM. Nanoparticles were collected by ultracentrifugation, washed with water and recovered by lyophilization.

Cytotoxicity measurements: Cytotoxicity was assessed in splenocytes using lactate dehydrogenase assay (LDH). Briefly, Splenocytes were cultured and treated with increasing concentration of GA functionalized liposomes at 1 μg/ml, 10 μg/ml or 100 μg/ml for 48 hours. The LDH reaction mixture was added and incubated at room temperature for approximately 10 minutes. The fluorescence was measured at Ex/Em 535/587 nm.

DiD staining: Liposomes were labeled with DiD during preparation. Briefly, when the lipid mixture was dissolved in the organic phase, 100 μl of 1 mg/mL DiD was added to the mixture at 10 μg of lipid, during liposome preparation by thin film rehydration. Liposomes were then prepared by thin film rehydration.

Transmission electron microscopy: Solutions of liposome (0.25 mM in water) were applied directly to a 200 mesh carbon coated copper grid (10 μL) for 30 s. Excess sample was blotted using filter paper. The grids were stained with uranyl acetate for 1 min and excess stain was removed using filter paper. Images were taken with a JEOL JEM-2100 transmission electron microscope (TEM) with an accelerating voltage of 200 kV.

In vivo administration of liposomes in mice: Both hind footpads of mice were injected with 15 μL of fluorescently labeled liposomes at 10 μg/mL.

Statistical analysis: Statistics were performed on results using a two way ANOVA with either Tukey or Bonferroni post-hoc analysis.

Example 1: Characterization of Mice Inbred Strains

Figure 1A:
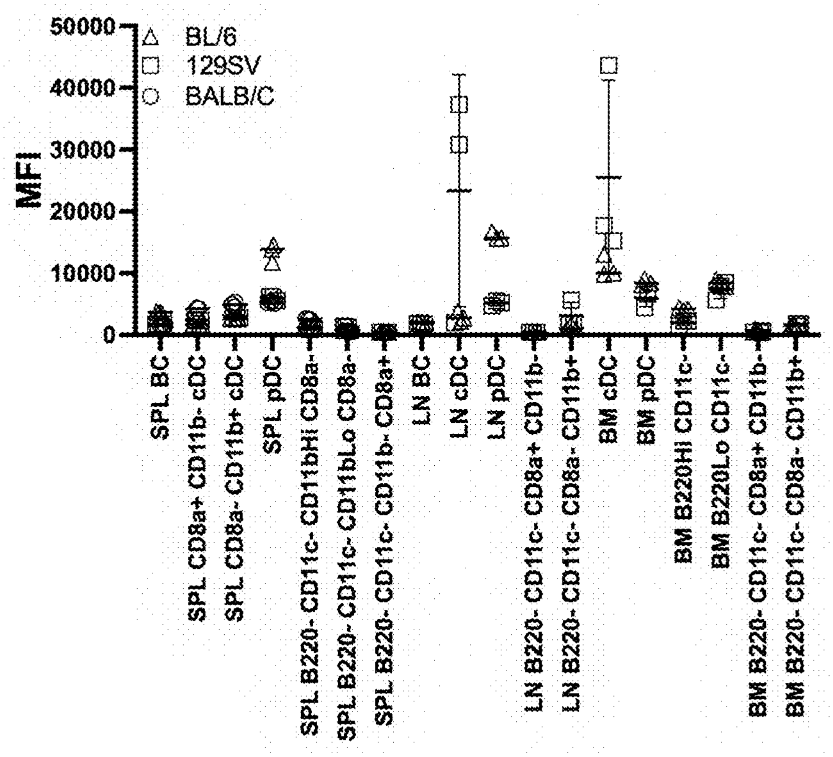
Figure 1B:
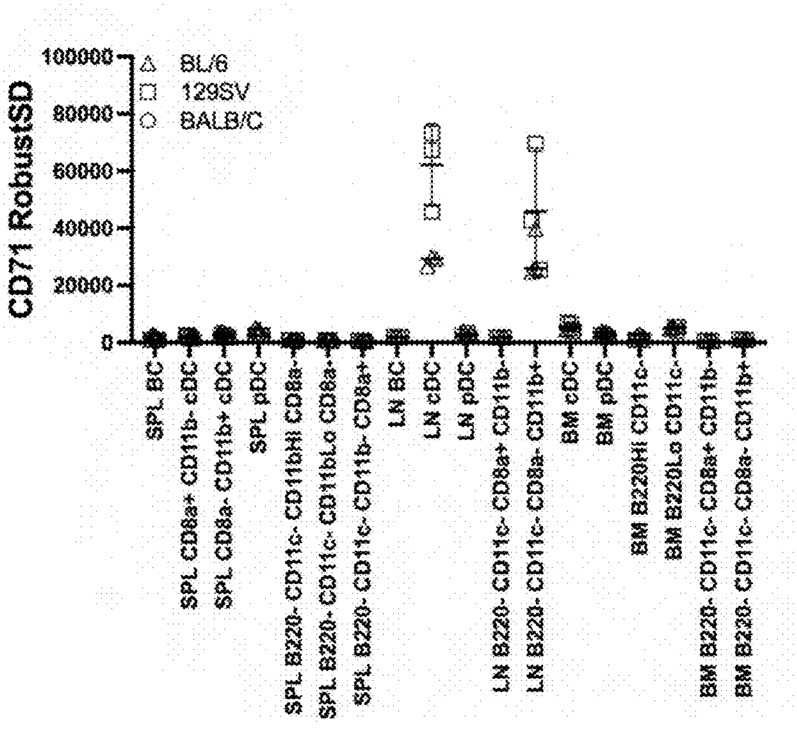
Figure 1C:
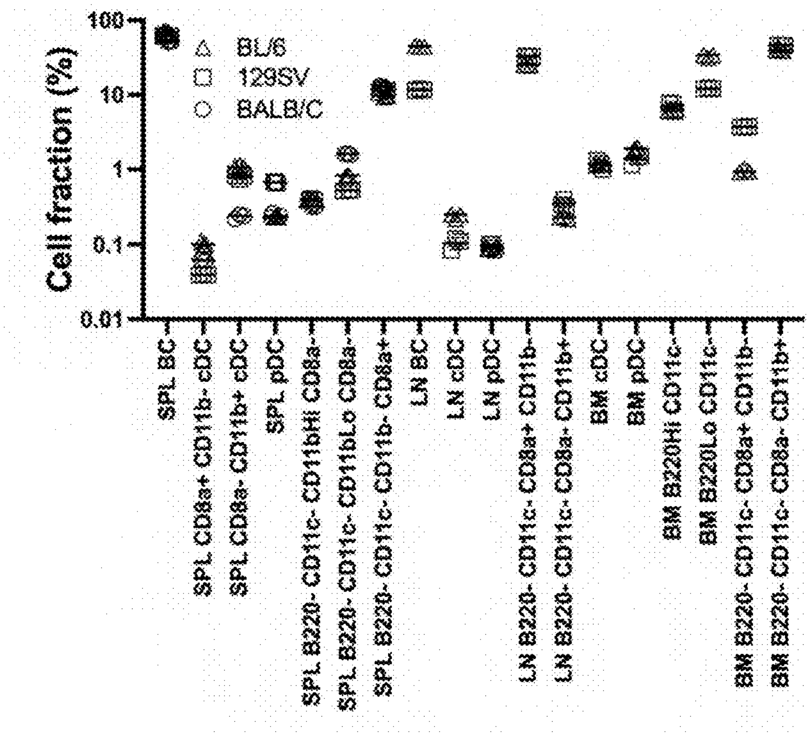
Figure 1D:
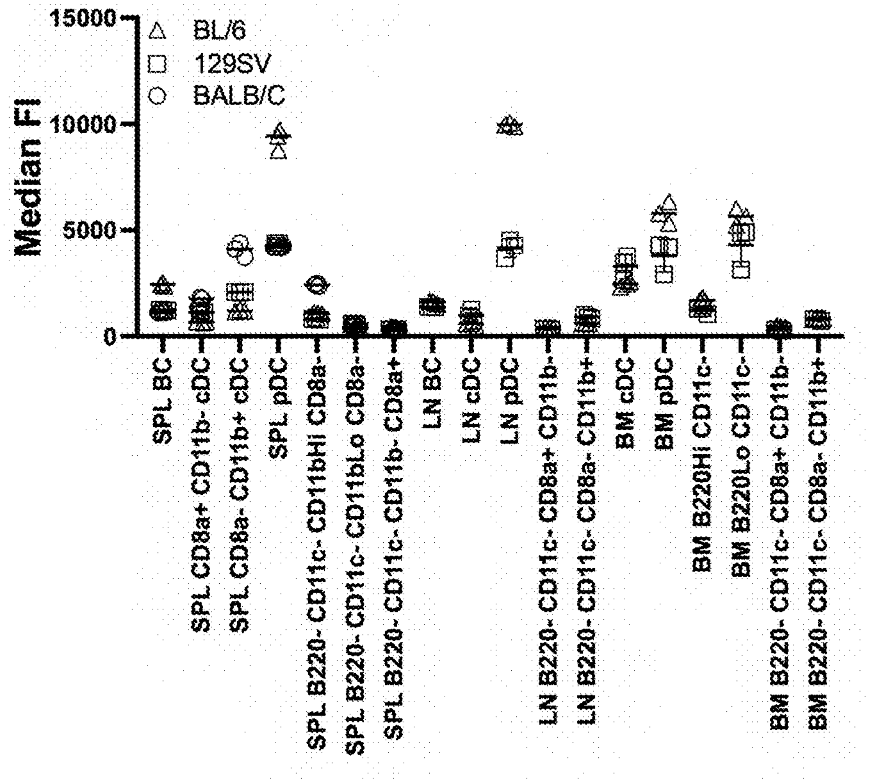
Figure 1E:
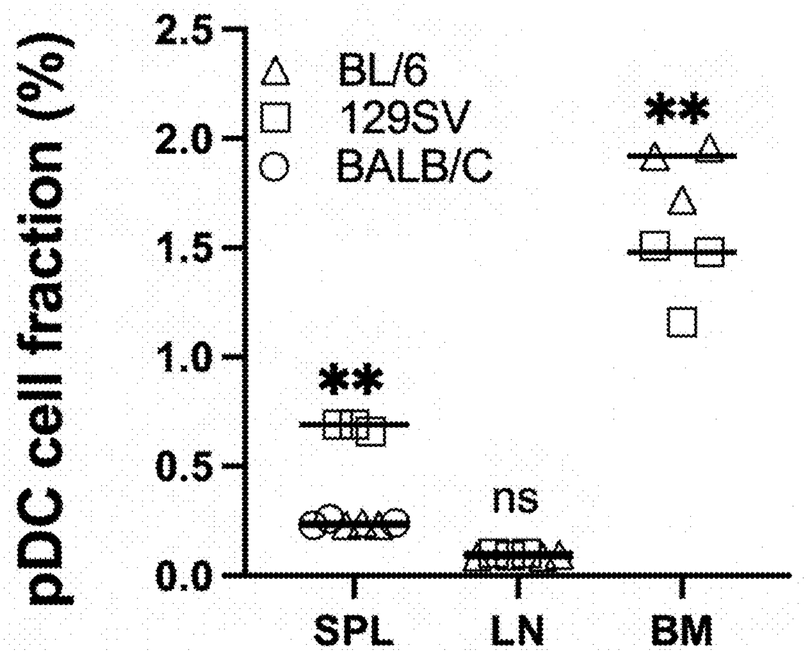
Figure 1F:
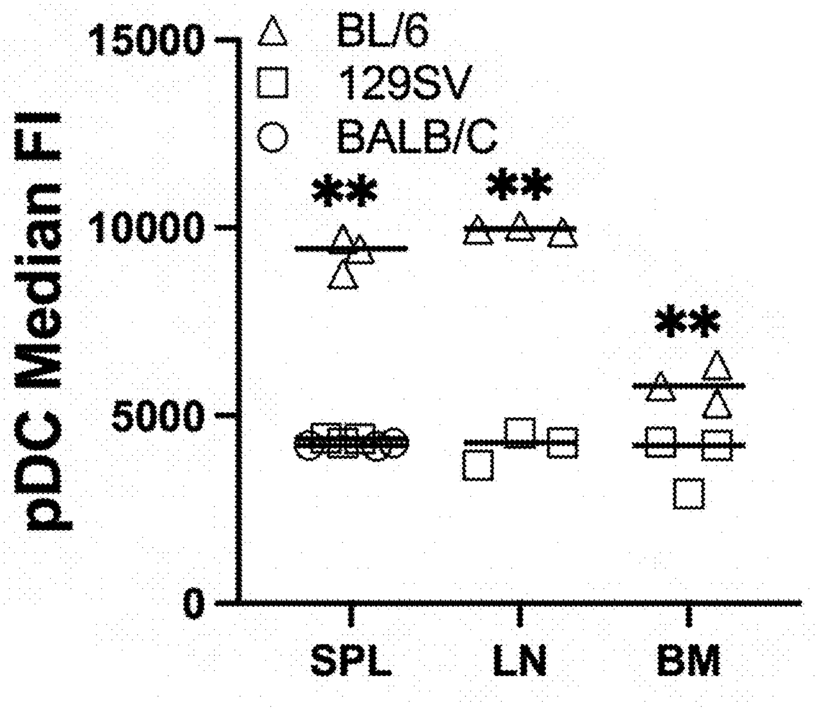

First, characterization of three inbred lines of mice, BL/6, 129SV, and BALB/C were undertaken to examine the pDC cell distribution and endogenous CD71 expression leukocytes in various tissues. Flow cytometric analyses showed that among the mice lines examined, BL/6 mice exhibited a medium level of pDCs fraction, especially in spleen and lymph node (FIG. 1A-1F). However, pDC fraction in BL/6 exhibited high expression CD71 (FIG. 1E-1F). Therefore, BL/6 mice were chosen for further analysis.

Figure 2A:
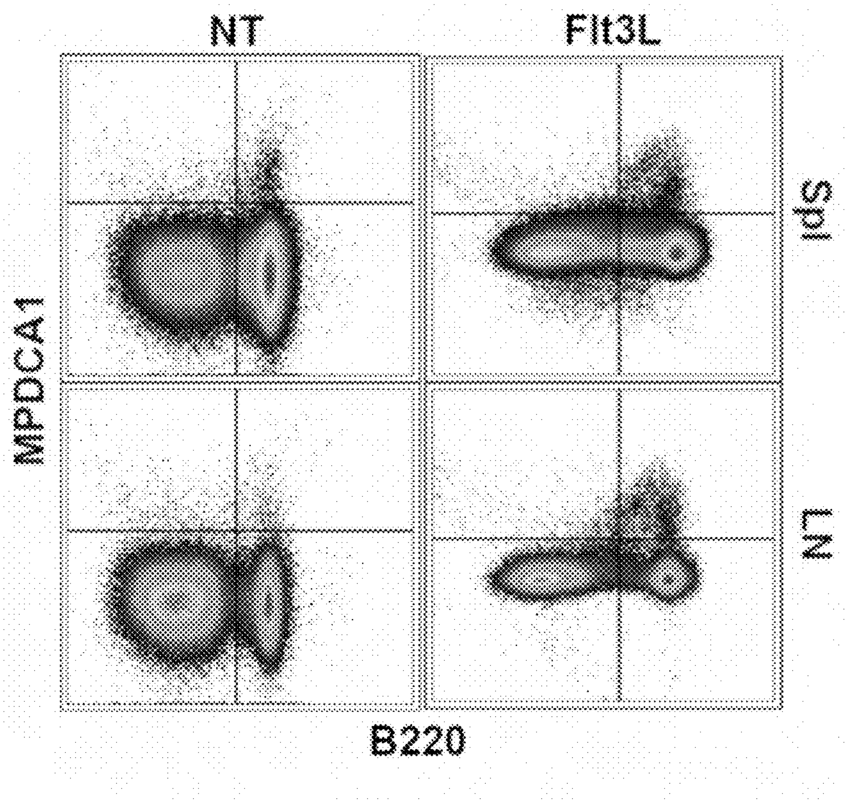
FIG. 2A-2B show inducible upregulation of pDC cell fraction following FLT3L injection over 7 days.
Figure 2B:
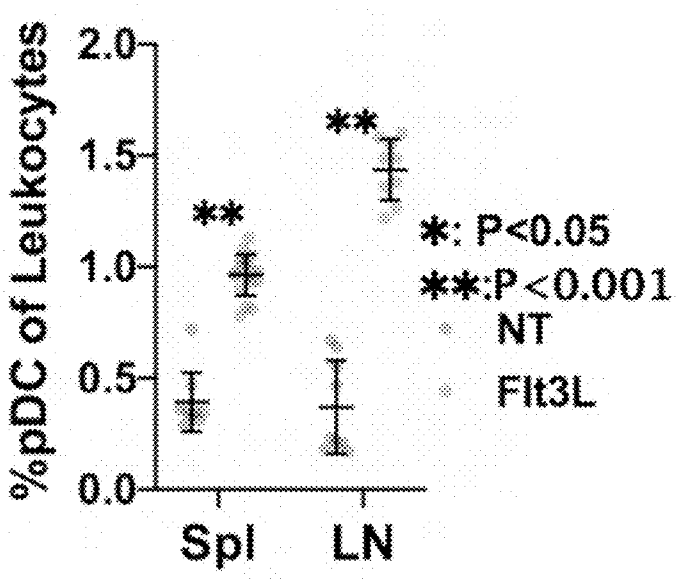
Figure 3A:
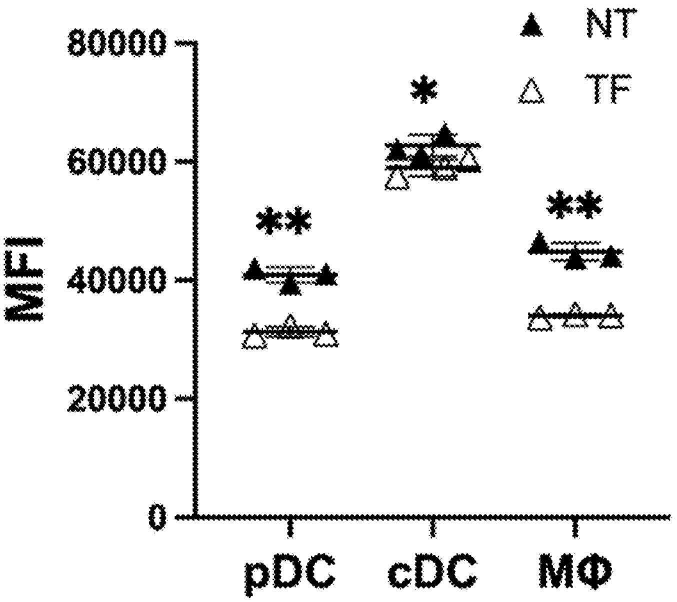
FIG. 3A-3B show effect of mouse transferrin on CD71 expression and pDC fraction after 7 days of BM differentiation culture. *$p<0.01$, **$p<0.001$, compared with cells not treated with transferrin, using two-way ANOVA.
Figure 3B:
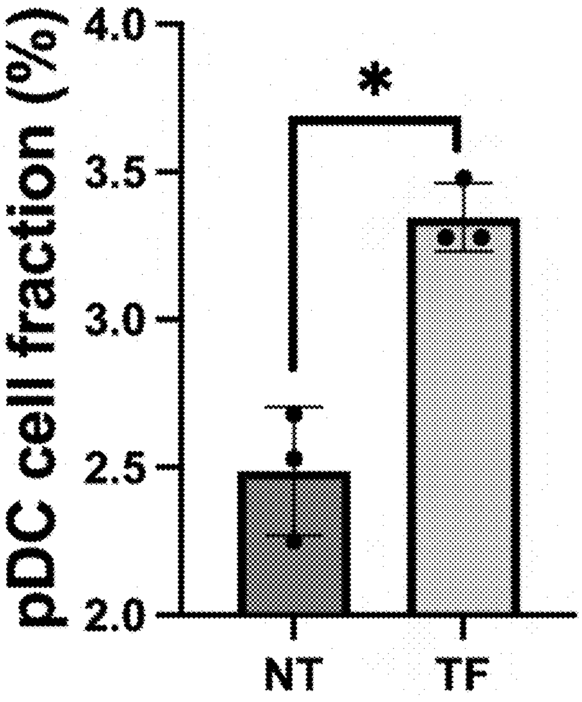

Further, the amount of pDC fraction was found inducible with injection of FMS-like tyrosine kinase 3 ligand in mice after 7 days (FIG. 2A-2B). Incubation of bone marrow differentiation culture with mouse transferrin for 7 days enhanced CD71 expression and pDC fraction (FIG. 2C-2D).

Example 2: Synthesis and Characterization of GA Functionalized Liposomes

GA-modified DSPE (1,2-distearoyl-sn-glycero-3-phosphorylethanolamine) was synthesized using copper catalyzed azide-alkynecyclo addition between GA-alkyne and DSPE-[PEG2000]-azide (FIG. 4A). DSPE-[PEG2000]-amine (FIG. 4A). GA functionalized liposomes (GALs) and unlabeled liposomes (ULs) loaded with the lipophilic dye DiD were formed using the thin-film rehydration method and characterized using dynamic light scattering (DLS) and transmission electron microscopy (TEM). TEM and DLS data showed GALs and ULs to be approximately 200 nm in diameter. The number frequency and mean diameter were found to be comparable between GALS and ULs (FIG. 4B-4D). Cytotoxicity of GA functionalized liposomes was measured in splenocyte using lactate dehydrogenase (LDH). It was observed that GA functionalized liposomes exerted minimal splenocyte toxicity even at high concentration, for a period of over 48 h (FIG. 5).

Uptake of GA functionalized liposomes was measured in single cell suspensions of mouse lymphoid tissue. Single cell suspensions were prepared using method shown in FIG. 6. using flow cytometry. Cells were gated sequentially to identify several populations of cells isolated from spleen, bone marrow and lymph node (FIG. 7). Based on CD11c, CD317, and B220, expression pDCs (B220+/CD11cint/CD317+),cDCs(B220-/CD11c+/CD317-) and B-cells (CD11c-/CD317-/B220+) were resolved. Uptake of GA functionalized liposomes were further assessed in cells from spleen, lymph node and bone marrow using DiD cell labeling. The percentage of DiD+cells were quantified for each tissue type over time. At 1,4 and 18 hours, liposomes are selectively taken up by pDCs in the spleen and lymph node (FIG. 8A-FIG. 8C). Kinetics of GAL-specific uptake observed were faster than phagocytosis. Nonspecific pDC uptake by cDCs was observed only after 18 hours. These results showed that GA functionalized liposomes specifically targeted pDC cells.

Uptake of GA functionalized liposomes was further assessed in the presence of transferrin. FIG. 9A-9F show that uptake of GA functionalized liposomes is only mildly reduced in lymph node and increased in spleen by the presence of transferrin. This showed that uptake of GA functionalized liposomes was largely noncompetitive with transferrin.

Example 3: GA Functionalized Nanoparticles

Alginate nanoparticles were prepared and functionalized with GA. Uptake of GA functionalized nanoparticles in cells from spleen, lymph node and bone marrow were assessed. The uptake of GA functionalized nanoparticles was found to be similar to that of GA functionalized liposomes (FIG. 10). This suggested that the targeting effect of GA is conserved with alginate nanoparticles.

Example 4: Distribution of GA Functionalized Liposomes In Vivo

Biodistribution of GA functionalized liposomes were studies in mice. FIG. 11 shows particle biodistribution in vivo 24 hours after footpad injection. GA functionalized liposomes were found in multiple tissues examined. Optimizations can be undertaken to target in-vivo biodistribution of GALs to avoid clearance through the liver and kidney and promote localization to the lymph nodes and spleen.

SUMMARY

The examples disclosed herein show that GALs were effective at targeting pDCs in mouse lymphoid tissue compared to other phagocytes. Data observed indicated a significant uptake of GALs by pDCs in the spleen and LN suspensions compared to cDCs or B cells. Addition of mouse transferrin had no significant impact on GAL uptake indicating minimal competition between GALs and CD71 mediated iron metabolism. LDH assay confirmed that GALs were not cytotoxic. This is significant because GALs loaded with appropriate cargo can be used for therapeutic targeting of pDCs in multiple disease models. In summary non-competitive delivery of liposomes disclosed herein can be applied for pDC targeted protein and vaccine delivery.

The invention claimed is:

1. A composition comprising liposomes, wherein the liposomes comprise gambogic acid-polyethylene glycol (PEG)-1,2-distearoyl-sn-glycero-3-phosphorylethanolamine (GA-PEG-DSPE).

2. The composition of claim 1, wherein the gambogic acid moiety enhances delivery of the liposomes to plasmacytoid dendritic cells.

3. The composition of claim 2, wherein the delivery of the liposomes to plasmacytoid dendritic cells is enhanced by at least by 25% compared to liposomes without the targeting moiety.

4. The composition of claim 1, wherein the liposomes further comprises a therapeutic agent or a diagnostic agent.

5. The composition of claim 4, wherein the therapeutic agent or diagnostic agent is a nucleic acid, an antiviral agent, an antibacterial agent, an antifungal agent, an antimetabolic agent, an anticancer agent, anti-inflammatory agent, a polypeptide, a protein, or an imaging agent.

6. The composition of claim 1, wherein the gambogic acid moiety binds to CD71 non-competitively with a natural ligand of CD71.

7. The composition of claim 1, wherein the gambogic acid moiety binds to CD71 non-competitively with transferrin.

8. The composition of claim 1, wherein the polyethylene glycol (PEG) moiety in the GA-PEG-DSPE has a molecular weight from about 750 Daltons to about 20,000 Daltons.

9. The composition of claim 8, wherein the PEG moiety has a molecular weight of from about 1000 Daltons to about 5000 Daltons.

10. The composition of claim 9, wherein the PEG moiety has a molecular weight of 2000 Daltons.

11. The composition of claim 10, wherein the GA-PEG-DSPE comprises a 1,2,3-triazole group.

12. The composition of claim 11, wherein the GA-PEG-DSPE has been made by reaction of alkyne-modified GA with azide-modified DSPE in a Cu (I) catalyzed click ligation.

13. A pharmaceutical composition comprising the composition of claim 1 and a pharmaceutically acceptable carrier.

14. A method of comprising administering an effective amount of the composition of claim 1 to a subject.

* * * * *